United States Patent
Komplin et al.

(10) Patent No.: US 9,527,788 B2
(45) Date of Patent: *Dec. 27, 2016

(54) METHODS FOR HYDROTHERMAL DIGESTION OF CELLULOSIC BIOMASS SOLIDS IN THE PRESENCE OF A DISTRIBUTED SLURRY CATALYST

(71) Applicant: SHELL OIL COMPANY, Houston, TX (US)

(72) Inventors: Glenn Charles Komplin, Katy, TX (US); Joseph Broun Powell, Houston, TX (US)

(73) Assignee: Shell Oil Company, Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/928,770

(22) Filed: Jun. 27, 2013

(65) Prior Publication Data

US 2014/0005444 A1   Jan. 2, 2014

Related U.S. Application Data

(60) Provisional application No. 61/665,627, filed on Jun. 28, 2012.

(51) Int. Cl.
*C07C 29/132* (2006.01)
*C13K 1/02* (2006.01)
*C10G 3/00* (2006.01)
*D21C 3/22* (2006.01)
*C10L 9/08* (2006.01)
*C10L 1/02* (2006.01)
*C10G 1/06* (2006.01)
*C10G 1/08* (2006.01)

(52) U.S. Cl.
CPC ............ *C07C 29/132* (2013.01); *C10G 1/065* (2013.01); *C10G 1/083* (2013.01); *C10G 3/42* (2013.01); *C10G 3/50* (2013.01); *C10L 1/02* (2013.01); *C10L 9/086* (2013.01); *C13K 1/02* (2013.01); *D21C 3/222* (2013.01); *C10L 2230/04* (2013.01); *Y02E 50/10* (2013.01); *Y02E 50/16* (2013.01); *Y02E 50/30* (2013.01); *Y02P 30/20* (2015.11); *Y02T 50/678* (2013.01)

(58) Field of Classification Search
None
See application file for complete search history.

(56) References Cited

U.S. PATENT DOCUMENTS

| | | |
|---|---|---|
| 3,347,741 A | 10/1967 | Hutchison |
| 4,104,113 A | 8/1978 | Sherman et al. |
| 5,116,475 A | 5/1992 | Edlund et al. |
| 5,565,061 A | 10/1996 | Salminen |
| 5,766,413 A | 6/1998 | Backlund et al. |
| 6,030,915 A | 2/2000 | de Boer |
| 6,123,807 A | 9/2000 | Engstrom et al. |
| 6,127,299 A | 10/2000 | de Boer et al. |
| 6,241,851 B1 | 6/2001 | Marcoccia |
| 2005/0274467 A1 | 12/2005 | Lawrence et al. |
| 2008/0050792 A1 | 2/2008 | Zmierezak et al. |
| 2008/0245496 A1 | 10/2008 | Kallmes |
| 2008/0312346 A1 | 12/2008 | McCall et al. |
| 2011/0282115 A1 | 11/2011 | Chedda et al. |
| 2011/0306804 A1* | 12/2011 | Cortright ...................... 568/861 |
| 2012/0151827 A1* | 6/2012 | Powell et al. .................. 44/307 |
| 2012/0152836 A1 | 6/2012 | Powell et al. |
| 2012/0156742 A1 | 6/2012 | Powell et al. |
| 2012/0157730 A1 | 6/2012 | Powell et al. |
| 2012/0172588 A1* | 7/2012 | Qiao et al. .................... 536/124 |
| 2012/0317872 A1 | 12/2012 | Powell et al. |
| 2012/0317873 A1 | 12/2012 | Johnson et al. |
| 2013/0109896 A1 | 5/2013 | Powell et al. |
| 2013/0152457 A1 | 6/2013 | Powell et al. |

(Continued)

FOREIGN PATENT DOCUMENTS

| | | |
|---|---|---|
| WO | 9945191 | 9/1999 |
| WO | WO2010025241 | 3/2010 |

(Continued)

OTHER PUBLICATIONS

International Search Report mailed Sep. 16, 2013, Ref. No. TH5283-PCT for Application No. PCT/US2013/048248 filed Jun. 27, 2013.

Huizenga, Huizenga et al., "Effect of Internal Filtration on Slurry Reactor Performance", Ing. Eng. Chem. Res. 38, 1999.

University of Missouri, Engineering Experiment Station Series, Plate No. 2—Autoclave and Filter Press, 1914, Issues 14-25(Google eBook), p. 21.

(Continued)

*Primary Examiner* — Karl J Puttlitz

(57) ABSTRACT

Digesting cellulosic biomass solids in the presence of a well-distributed slurry catalyst capable of activating molecular hydrogen may limit the amount of degradation products that form during digestion. Methods for digesting cellulosic biomass solids can comprise: providing cellulosic biomass solids and a slurry catalyst in a hydrothermal digestion unit, the slurry catalyst being capable of activating molecular hydrogen; distributing the slurry catalyst within the cellulosic biomass solids using upwardly directed fluid flow in the hydrothermal digestion unit; heating the cellulosic biomass solids in the hydrothermal digestion unit in the presence of the slurry catalyst, a digestion solvent, and molecular hydrogen, thereby forming a liquor phase comprising soluble carbohydrates; and performing a first catalytic reduction reaction on the soluble carbohydrates within the hydrothermal digestion unit, thereby at least partially forming a reaction product comprising a triol, a diol, a monohydric alcohol, or any combination thereof in the hydrothermal digestion unit.

31 Claims, No Drawings

(56) References Cited

U.S. PATENT DOCUMENTS

2013/0152458 A1    6/2013    Powell et al.

FOREIGN PATENT DOCUMENTS

| WO | WO2012082367 | 6/2012 |
| WO | 2013089796 | 6/2013 |
| WO | WO2013089796 | 6/2013 |
| WO | WO2013089797 | 6/2013 |
| WO | WO2013089798 | 6/2013 |
| WO | WO2013089799 | 6/2013 |

OTHER PUBLICATIONS

Parr Catalogue; "Stirred Reactors and Pressure Vessels"; vol. 9; pp. 1, 16 and 24-29; printed Feb. 3, 2016.

* cited by examiner

METHODS FOR HYDROTHERMAL DIGESTION OF CELLULOSIC BIOMASS SOLIDS IN THE PRESENCE OF A DISTRIBUTED SLURRY CATALYST

This present application claims the benefit of U.S. Patent Application No. 61/665,627, filed Jun. 28, 2012, the entire disclosure of which is hereby incorporated by reference.

FIELD OF THE INVENTION

The present disclosure generally relates to digestion, and, more specifically, to methods for distributing a slurry catalyst within cellulosic biomass Solids During Hydrothermal Digestion.

BACKGROUND OF THE INVENTION

A number of substances of commercial significance may be produced from natural sources, including biomass. Cellulosic biomass may be particularly advantageous in this regard due to the versatility of the abundant carbohydrates found therein in various forms. As used herein, the term "cellulosic biomass" refers to a living or recently living biological material that contains cellulose. The lignocellulosic material found in the cell walls of higher plants is the world's largest source of carbohydrates. Materials commonly produced from cellulosic biomass may include, for example, paper and pulpwood via partial digestion, and bioethanol by fermentation.

Plant cell walls are divided into two sections: primary cell walls and secondary cell walls. The primary cell wall provides structural support for expanding cells and contains three major polysaccharides (cellulose, pectin, and hemicellulose) and one group of glycoproteins. The secondary cell wall, which is produced after the cell has finished growing, also contains polysaccharides and is strengthened through polymeric lignin that is covalently crosslinked to hemicellulose. Hemicellulose and pectin are typically found in abundance, but cellulose is the predominant polysaccharide and the most abundant source of carbohydrates. The complex mixture of constituents that is co-present with the cellulose can make its processing difficult, as discussed hereinafter.

Significant attention has been placed on developing fossil fuel alternatives derived from renewable resources. Cellulosic biomass has garnered particular attention in this regard due to its abundance and the versatility of the various constituents found therein, particularly cellulose and other carbohydrates. Despite promise and intense interest, the development and implementation of bio-based fuel technology has been slow. Existing technologies have heretofore produced fuels having a low energy density (e.g., bioethanol) and/or that are not fully compatible with existing engine designs and transportation infrastructure (e.g., methanol, biodiesel, Fischer-Tropsch diesel, hydrogen, and methane). An energy- and cost-efficient process for processing cellulosic biomass into fuel blends having similar compositions to fossil fuels would be highly desirable to address the foregoing issues and others.

When converting cellulosic biomass into fuel blends and other materials, cellulose and other complex carbohydrates therein can be extracted and transformed into simpler organic molecules, which can be further reformed thereafter. Fermentation is one process whereby complex carbohydrates from biomass may be converted into a more usable form. However, fermentation processes are typically slow, require large volume reactors, and produce an initial reaction product having a low energy density (ethanol). Digestion is another way in which cellulose and other complex carbohydrates may be converted into a more usable form. Digestion processes can break down cellulose and other complex carbohydrates within cellulosic biomass into simpler, soluble carbohydrates that are suitable for further transformation through downstream reforming reactions. As used herein, the term "soluble carbohydrates" refers to monosaccharides or polysaccharides that become solubilized in a digestion process. Although the underlying chemistry is understood behind digesting cellulose and other complex carbohydrates and further transforming simple carbohydrates into organic compounds reminiscent of those present in fossil fuels, high-yield and energy-efficient digestion processes suitable for converting cellulosic biomass into fuel blends have yet to be developed. In this regard, the most basic requirement associated with converting cellulosic biomass into fuel blends using digestion and other processes is that the energy input needed to bring about the conversion should not be greater than the available energy output of the product fuel blends. This basic requirement leads to a number of secondary issues that collectively present an immense engineering challenge that has not been solved heretofore.

The issues associated with converting cellulosic biomass into fuel blends in an energy- and cost-efficient manner using digestion are not only complex, but they are entirely different than those that are encountered in the digestion processes commonly used in the paper and pulpwood industry. Since the intent of cellulosic biomass digestion in the paper and pulpwood industry is to retain a solid material (e.g., wood pulp), incomplete digestion is usually performed at low temperatures (e.g., less than about 100° C.) for a fairly short period of time. In contrast, digestion processes suitable for converting cellulosic biomass into fuel blends and other materials are ideally configured to maximize yields by solubilizing as much of the original cellulosic biomass charge as possible in a high-throughput manner.

Production of greater quantities of soluble carbohydrates for use in fuel blends and other materials via routine modification of paper and pulpwood digestion processes is not feasible for a number of reasons. Simply running the digestion processes of the paper and pulpwood industry for a longer period of time to produce more soluble carbohydrates is undesirable from a throughput standpoint. Use of digestion promoters such as strong alkalis, strong acids, or sulfites to accelerate the digestion rate can increase process costs and complexity due to post-processing separation steps and the possible need to protect downstream components from these agents. Accelerating the digestion rate by increasing the digestion temperature can actually reduce yields due to thermal degradation of soluble carbohydrates that can occur at elevated digestion temperatures, particularly over extended periods of time. Once produced by digestion, soluble carbohydrates are very reactive and can rapidly degrade to produce caramelans and other heavy ends degradation products, especially under higher temperature conditions, such as above about 150° C. Use of higher digestion temperatures can also be undesirable from an energy efficiency standpoint. Any of these difficulties can defeat the economic viability of fuel blends derived from cellulosic biomass.

One way in which soluble carbohydrates can be protected from thermal degradation is through subjecting them to one or more catalytic reduction reactions, which may include hydrogenation and/or hydrogenolysis reactions. Stabilizing soluble carbohydrates through conducting one or more catalytic reduction reactions may allow digestion of cellulosic biomass to take place at higher temperatures than would otherwise be possible without unduly sacrificing yields. Reaction products comprising triols, diols, monohydric alcohols, and any combination thereof may be produced as a result of performing one or more catalytic reduction reactions on soluble carbohydrates. These reaction products may be readily transformable into fuel blends and other materials through downstream reforming reactions. In addition, the above reaction products are good solvents in which a hydrothermal digestion may be performed. Use of such solvents, which may include monohydric alcohols, glycols, and ketones, for example, may accelerate digestion rates and aid in stabilizing other components of cellulosic biomass, such as lignins, for example, which can otherwise agglomerate and foul process equipment. Separation and recycle of a solvent can sometimes require input of extensive amounts of energy, which can reduce the net energy output available from fuel blends derived from cellulosic biomass. By using the reaction product as a solvent, the net energy output of the fuel blends may be increased due to a reduced need for separation steps to take place.

Another issue associated with the processing of cellulosic biomass into fuel blends and other materials is created by the need for high conversion percentages of a cellulosic biomass charge into soluble carbohydrates. Specifically, as cellulosic biomass solids are digested, their size gradually decreases to the point that they can become fluidly mobile. As used herein, cellulosic biomass solids that are fluidly mobile, particularly cellulosic biomass solids that are about 3 mm in size or less, will be referred to as "cellulosic biomass fines." Cellulosic biomass fines can be transported out of a digestion zone of a system for converting cellulosic biomass and into one or more zones where solids are unwanted and can be detrimental. For example, cellulosic biomass fines have the potential to plug catalyst beds, transfer lines, and the like. Furthermore, although small in size, cellulosic biomass fines may represent a non-trivial fraction of the cellulosic biomass charge, and if they are not further converted into soluble carbohydrates, the ability to attain a satisfactory conversion percentage may be impacted. Since the digestion processes of the paper and pulpwood industry are run at relatively low cellulosic biomass conversion percentages, smaller amounts of cellulosic biomass fines are believed to be generated and have a lesser impact on those digestion processes.

In addition to the desired carbohydrates, other substances may be present within cellulosic biomass that can be especially problematic to deal with in an energy- and cost-efficient manner. Sulfur- and/or nitrogen-containing amino acids or other catalyst poisons may be present in cellulosic biomass. If not removed, these catalyst poisons can impact the catalytic reduction reaction(s) used to stabilize soluble carbohydrates, thereby resulting in process downtime for catalyst regeneration and/or replacement and reducing the overall energy efficiency when restarting the process. On the other hand, in-process removal of these catalyst poisons can also impact the energy efficiency of the biomass conversion process, since the ion-exchange processes typically needed to affect their removal are usually conducted at temperatures below those at which soluble carbohydrates are produced by digestion, thereby introducing heat exchange operations that add to design complexity and may increase operational costs. In addition to catalyst poisons, lignin, which is a non-cellulosic biopolymer, may become solubilized in conjunction with the production of soluble carbohydrates. If not addressed in some manner, lignin concentrations may become sufficiently high during biomass conversion that precipitation eventually occurs, thereby resulting in costly system downtime. In the alternative, some lignin may remain unsolubilized, and costly system downtime may eventually be needed to affect its removal.

As evidenced by the foregoing, the efficient conversion of cellulosic biomass into fuel blends is a complex problem that presents immense engineering challenges. The present disclosure addresses these challenges and provides related advantages as well.

SUMMARY OF THE INVENTION

The present disclosure generally relates to digestion, and, more specifically, to methods for distributing a slurry catalyst within cellulosic biomass solids during hydrothermal digestion.

In some embodiments, the present disclosure provides a method comprising: providing cellulosic biomass solids and a slurry catalyst in a hydrothermal digestion unit, the slurry catalyst being capable of activating molecular hydrogen ("Molecular Hydrogen Activating Slurry Catalyst"); distributing the slurry catalyst within the cellulosic biomass solids using upwardly directed fluid flow in the hydrothermal digestion unit; heating the cellulosic biomass solids in the hydrothermal digestion unit in the presence of the slurry catalyst, a digestion solvent, and molecular hydrogen, thereby forming a liquor phase comprising soluble carbohydrates; and performing a first catalytic reduction reaction on the soluble carbohydrates within the hydrothermal digestion unit, thereby at least partially forming a reaction product comprising a triol, a diol, a monohydric alcohol, or any combination thereof in the hydrothermal digestion unit.

In some embodiments, the present disclosure provides a method comprising: providing cellulosic biomass solids and a slurry catalyst in a hydrothermal digestion unit, the slurry catalyst being capable of activating molecular hydrogen ("Molecular Hydrogen Activating Slurry Catalyst"); heating the cellulosic biomass solids in the hydrothermal digestion unit in the presence of molecular hydrogen while circulating the slurry catalyst through the cellulosic biomass solids in a digestion solvent, thereby forming a liquor phase comprising soluble carbohydrates; and performing a first catalytic reduction reaction on the soluble carbohydrates within the hydrothermal digestion unit, thereby at least partially forming a reaction product comprising a triol, a diol, a monohydric alcohol, or any combination thereof in the hydrothermal digestion unit.

The features and advantages of the present disclosure will be readily apparent to one having ordinary skill in the art upon a reading of the description of the embodiments that follows.

DETAILED DESCRIPTION

The present disclosure generally relates to digestion, and, more specifically, to methods for distributing a slurry catalyst within cellulosic biomass solids during hydrothermal digestion.

In the embodiments described herein, the digestion rate of cellulosic biomass solids may be accelerated in the presence of a digestion solvent. In some instances, the digestion solvent may be maintained at elevated pressures that keep the digestion solvent in a liquid state above its normal boiling point. Although the more rapid digestion rate of cellulosic biomass solids under these types of conditions may be desirable from the standpoint of throughput, soluble carbohydrates may be susceptible to degradation at elevated temperatures, as discussed above.

To combat the problems associated with degradation of soluble carbohydrates, the present disclosure provides methods for digesting cellulosic biomass solids while effectively promoting the thermal stabilization of soluble carbohydrates produced therefrom. Specifically, the present disclosure provides methods whereby hydrothermal digestion and one or more catalytic reduction reactions take place in the same vessel. We have found that stabilization of soluble carbohydrates occurs most effectively if conducted in this manner. The foregoing may be accomplished by including a slurry catalyst capable of activating molecular hydrogen within a hydrothermal digestion unit containing cellulosic biomass solids and transporting the slurry catalyst in the digesting liquor phase to affect its distribution therein. As used herein, the term "slurry catalyst" refers to a catalyst comprising fluidly mobile catalyst particles that can be at least partially suspended in a fluid phase via gas flow, liquid flow, mechanical agitation, or any combination thereof. The presence of the slurry catalyst within the hydrothermal digestion unit may allow one or more in situ catalytic reduction reactions to take place therein, thereby advantageously intercepting and transforming soluble carbohydrates into a more stable reaction product as soon as feasible after the soluble carbohydrates form. As used herein, the term "in situ catalytic reduction reaction" refers to a catalytic reduction reaction that occurs in the same vessel as a digestion process. Formation of the reaction product may reduce the amount of thermal decomposition that occurs during hydrothermal digestion, thereby enabling high yield conversion of cellulosic biomass solids into a desired reaction product to take place in a timely manner.

In addition to rapidly stabilizing soluble carbohydrates as a reaction product, conducting one or more in situ catalytic reduction reactions may also be particularly advantageous from an energy efficiency standpoint. Specifically, the hydrothermal digestion of cellulosic biomass is an endothermic process, whereas catalytic reduction reactions are exothermic. Thus, the excess heat generated by the in situ catalytic reduction reaction(s) may be utilized to drive the hydrothermal digestion, thereby lowering the amount of additional heat energy input needed to conduct digestion. Since digestion and catalytic reduction take place within the same vessel in the embodiments described herein, there is minimal opportunity for heat transfer loss to take place, as would occur if the catalytic reduction reaction(s) were to be conducted in a separate location. In addition, in such a configuration, the in situ catalytic reduction reaction(s) may provide a growing supply of the reaction product within the hydrothermal digestion unit, which may serve as and/or replenish the digestion solvent. Since the reaction product and the digestion solvent may be the same, there is no express need to separate and recycle a majority of the digestion solvent before further processing the reaction product downstream, which may be further advantageous from an energy efficiency standpoint, as discussed above.

Although conducting one or more in situ catalytic reduction reactions may be particularly advantageous from an energy efficiency standpoint and for purposes of stabilizing soluble carbohydrates, successfully executing such a coupled process may be problematic in other aspects. One significant issue that may be encountered is that of catalyst distribution within the digesting cellulosic biomass solids. Without adequate catalyst distribution being realized, ineffective stabilization of soluble carbohydrates may occur. Specifically, soluble carbohydrates may have a greater opportunity to thermally degrade during the time they take to reach a catalytic site and undergo catalytic reduction. In contrast, by having a well distributed catalyst, the soluble carbohydrates produced during digestion may be less removed from a catalytic site and can be stabilized more readily. Although a catalyst might be pre-mixed with cellulosic biomass solids or co-blended with cellulosic biomass solids being added to a hydrothermal digestion unit, these solutions may produce inadequate catalyst distribution and present significant engineering challenges that markedly increase process complexity and operational costs.

In the methods described herein, a slurry catalyst may be distributed within cellulosic biomass solids using fluid flow to convey the slurry catalyst therein. Although the slurry catalyst may be conveyed into the cellulosic biomass solids using fluid flow from any direction within the hydrothermal digestion unit, we consider it most effective to utilize upwardly directed fluid flow to convey the slurry catalyst into the cellulosic biomass solids. Conveying the slurry catalyst into a cellulosic biomass charge from bottom to top using upwardly directed fluid flow may present a number of advantages. Specifically, it may overcome settling and gravity-induced compaction that occurs during the addition and digestion of cellulosic biomass solids. Settling and compaction of cellulosic biomass solids may impact fluid flow through the hydrothermal digestion unit and particularly reduce one's ability to effectively distribute a slurry catalyst therein. By using upwardly directed fluid flow, settling and compaction issues may be reduced through promoting expansion of the cellulosic biomass charge to allow the slurry catalyst to become distributed therein. In addition, by using upwardly directed fluid flow, there may be a reduced need to use mechanical stirring or like means of mechanical agitation that might otherwise be needed to obtain an adequate catalyst distribution. This feature may allow high loadings of cellulosic biomass solids relative to digestion solvent to be used, thereby improving throughput and process economics.

Use of upwardly directed fluid flow to distribute a slurry catalyst within cellulosic biomass solids may allow higher loadings of cellulosic biomass solids relative to digestion solvent to be used than would otherwise be possible with other modes of catalyst distribution. The relatively large size of most cellulosic biomass solids (e.g., about 1 mm or greater) may produce interstitial voids within a packed or expanded bed of cellulosic biomass solids in which a slurry catalyst may be distributed even at high ratios of cellulosic biomass solids relative to the digestion solvent. At high ratios of cellulosic biomass solids relative to digestion solvent (e.g., about 10% cellulosic biomass solids relative to solvent or greater), a viscous paste can form, particularly when the biomass particulate size is small, which may be difficult to mechanically stir or otherwise mechanically agitate. The embodiments described herein take advantage of the natural bed porosity of cellulosic biomass solids in order to distribute a slurry catalyst therein without the need for mechanical stirring or like mixing. The ability to utilize high loadings of cellulosic biomass solids relative to digestion solvent in the present embodiments may be advantageous from a throughput standpoint. Specifically, larger amounts of cellulosic biomass solids may be processed per unit size of the hydrothermal digestion unit, thereby improving process economics. Further, smaller volume digestion units, which may be simpler to construct and maintain, may also be used without sacrificing throughput, thereby further aiding process economics.

When using upwardly directed fluid flow to convey a slurry catalyst into cellulosic biomass solids, proper distribution of the slurry catalyst is not necessarily a guaranteed outcome, although this issue may be addressed in several different fashions, as discussed hereinafter. Retention of a slurry catalyst in a defined location is one issue that is commonly encountered in the art. Of relevance to the present embodiments, a slurry catalyst being conveyed by upwardly directed fluid flow may traverse completely through cellulosic biomass solids before digestion is finished and collect above the cellulosic biomass solids where the catalyst serves no effective stabilization purpose. One solution to this issue is described in commonly owned, co-pending U.S. Patent Application 61/665,727, filed Jun. 28, 2012 entitled "Methods for Hydrothermal Digestion of Cellulosic Biomass Solids in the Presence of a Slurry Catalyst and a Digestible Filter Aid," filed concurrently herewith and incorporated herein by reference in its entirety, which describes that cellulosic biomass solids may at least partially retain slurry catalyst particulates therein, and the degree of retention may be changed by modulating the size of at least some of the cellulosic biomass solids being added to the hydrothermal digestion unit.

Another technique for retaining a slurry catalyst within cellulosic biomass solids is to carefully adjust the velocity of upwardly directed fluid flow such that the slurry catalyst particulates are only fluidized to a certain height within a cellulosic biomass charge. As one of ordinary skill in the art will recognize, fluid flow dynamics dictate that smaller slurry catalyst particulates are fluidized to a greater extent and travel to a greater height than do larger particulates. Thus, in some embodiments, the velocity of the upwardly directed fluid flow may be adjusted so that a population of slurry catalyst particulates is distributed throughout the height of a given cellulosic biomass charge. One difficulty associated with this approach is the selection of a population of slurry catalyst particulates having a size range compatible with the upwardly directed fluid flow velocity, such that an acceptable degree of slurry catalyst distribution occurs. Specifically, for a given slurry catalyst population, the lower portion of a cellulosic biomass charge may be devoid of slurry catalyst if the upwardly directed fluid flow velocity is too high. Conversely, if the upwardly directed fluid flow velocity is too low, the upper portion of a cellulosic biomass charge may be devoid of the slurry catalyst. In some instances, there may be limited opportunities to alter the upwardly directed fluid flow velocity. Although a population of slurry catalyst particulates may be prepared with a designed size range so as to be compatible with a given velocity of upwardly directed fluid flow, this represents a complex and potentially costly engineering solution. Furthermore, using a designed size range for the slurry catalyst may limit opportunities to make additional process modifications.

In still another approach, one can make no attempt to actively retain the slurry catalyst within the cellulosic biomass solids. Instead, the slurry catalyst can be activately circulated through the cellulosic biomass solids at an upwardly directed fluid flow velocity sufficient to transport at least a portion of the slurry catalyst particulates therethrough. Slurry catalyst particulates traversing through the cellulosic biomass solids may then be recirculated to bottom of the cellulosic biomass charge for another pass therethrough.

Forcing the slurry catalyst to circulate within the cellulosic biomass solids may be advantageous from a number of standpoints. First, sufficiently rapid velocities of upwardly directed fluid flow may reduce thermal gradients within the hydrothermal digestion unit that can otherwise occur. In addition, forced circulation can reduce the need to rigorously control the velocity of upwardly directed fluid flow to be compatible with a given population of slurry catalyst particulates. Lessening the need to rigorously control the velocity of upwardly directed fluid flow may also advantageously allow process modifications to be more readily made, including supplementing the return flow of the slurry catalyst with additional fluid streams. Furthermore, forced circulation of the slurry catalyst may ensure that the catalyst is distributed throughout the entirety of the cellulosic biomass charge, thereby promoting stabilization of the reaction product produced in all regions of the digestion unit.

Another advantage of forcing the slurry catalyst to circulate within the cellulosic biomass solids is that the circulation may also address the problem of cellulosic biomass fines. Specifically, in some embodiments described herein, cellulosic biomass fines may be conveyed along with the circulating slurry catalyst. Although migration of cellulosic biomass fines would ordinarily be undesirable, in this case migration is actually advantageous, since the cellulosic biomass fines may be re-introduced to the hydrothermal digestion unit with the return flow of the slurry catalyst. Thereafter, further digestion of the cellulosic biomass fines may occur, thereby potentially increasing yields.

Even with forced circulation of the slurry catalyst through a packed or expanded charge of cellulosic biomass solids, some of the slurry catalyst may be retained by the cellulosic biomass solids. Retention of the slurry catalyst within the cellulosic biomass solids may increase the average concentration of the slurry catalyst within a region in which hydrothermal digestion is taking place, thereby further enhancing the rate of catalytic stabilization of soluble carbohydrates produced during digestion. The increased average concentration may reduce the flow rate needed for effective distribution of the slurry catalyst to take place.

Although conducting one or more in situ catalytic reduction reactions can be highly desirable for the purposes of stabilizing soluble carbohydrates and achieving heat integration, the catalyst poisons and other substances within cellulosic biomass may make implementing such a process very difficult. When conducting an in situ catalytic reduction reaction, there is no opportunity to remove catalyst poisons before they contact the distributed slurry catalyst. One way in which this issue can be addressed is to use a poison-tolerant slurry catalyst, some of which are discussed hereinbelow. Another alternative is to use a slurry catalyst that is regenerable upon exposure to conditions that can be readily established in or near the hydrothermal digestion unit. For example, in some embodiments, a regenerable slurry catalyst may be regenerated through exposure to water at a temperature of at least about 300° C.

Still another alternative to address the issue of catalyst poisoning is to conduct the digestion of the cellulosic biomass solids in stages. Many of the poisons that may deactivate a slurry catalyst arise from sulfur- and nitrogen-containing compounds in the raw cellulosic biomass solids, particularly amino acids. Sulfur- and nitrogen-containing compounds, along with hemicellulose and lignin, may be at least partially removed from cellulosic biomass solids at lower digestion temperatures than those at which cellulose produces soluble carbohydrates. By controlling the digestion temperature, a biomass pulp may be produced that is enriched in cellulose but depleted in catalyst poisons that may undesirably affect the catalytic activity, thereby allowing hydrothermal digestion of the biomass pulp to take place with a lesser impact on catalytic activity.

Unless otherwise specified herein, it is to be understood that use of the terms "biomass" or "cellulosic biomass" in the description herein refers to "cellulosic biomass solids." Solids may be in any size, shape, or form. The cellulosic biomass solids may be natively present in any of these solid sizes, shapes, or forms, or they may be further processed prior to hydrothermal digestion. In some embodiments, the cellulosic biomass solids may be chopped, ground, shredded, pulverized, and the like to produce a desired size prior to hydrothermal digestion. In some or other embodiments, the cellulosic biomass solids may be washed (e.g., with water, an acid, a base, combinations thereof, and the like) prior to hydrothermal digestion taking place.

In practicing the present embodiments, any type of suitable cellulosic biomass source may be used. Suitable cellulosic biomass sources may include, for example, forestry residues, agricultural residues, herbaceous material, municipal solid wastes, waste and recycled paper, pulp and paper mill residues, and any combination thereof. Thus, in some embodiments, a suitable cellulosic biomass may include, for example, corn stover, straw, bagasse, miscanthus, sorghum residue, switch grass, bamboo, water hyacinth, hardwood, hardwood chips, hardwood pulp, softwood, softwood chips, softwood pulp, and any combination thereof. Leaves, roots, seeds, stalks, husks, and the like may be used as a source of the cellulosic biomass. Common sources of cellulosic biomass may include, for example, agricultural wastes (e.g., corn stalks, straw, seed hulls, sugarcane leavings, nut shells, and the like), wood materials (e.g., wood or bark, sawdust, timber slash, mill scrap, and the like), municipal waste (e.g., waste paper, yard clippings or debris, and the like), and energy crops (e.g., poplars, willows, switch grass, alfalfa, prairie bluestream, corn, soybeans, and the like). The cellulosic biomass may be chosen based upon considerations such as, for example, cellulose and/or hemicellulose content, lignin content, growing time/season, growing location/transportation cost, growing costs, harvesting costs, and the like.

Illustrative carbohydrates that may be present in cellulosic biomass solids include, for example, sugars, sugar alcohols, celluloses, lignocelluloses, hemicelluloses, and any combination thereof. Once soluble carbohydrates have been produced through hydrothermal digestion according to the embodiments described herein, the soluble carbohydrates may be transformed into a more stable reaction product comprising a triol, a diol, a monohydric alcohol, or any combination thereof via one or more catalytic reduction reactions. In some embodiments, the reaction product may be further reformed into a biofuel using any combination of further hydrogenolysis reactions and/or hydrogenation reactions, condensation reactions, isomerization reactions, oligomerization reactions, hydrotreating reactions, alkylation reactions, and the like.

In some embodiments, methods described herein can comprise: providing cellulosic biomass solids and a slurry catalyst in a hydrothermal digestion unit, the slurry catalyst being capable of activating molecular hydrogen; distributing the slurry catalyst within the cellulosic biomass solids using upwardly directed fluid flow in the hydrothermal digestion unit; heating the cellulosic biomass solids in the hydrothermal digestion unit in the presence of the slurry catalyst, a digestion solvent, and molecular hydrogen, thereby forming a liquor phase comprising soluble carbohydrates; and performing a first catalytic reduction reaction on the soluble carbohydrates within the hydrothermal digestion unit, thereby at least partially forming a reaction product comprising a triol, a diol, a monohydric alcohol, or any combination thereof in the hydrothermal digestion unit.

In some embodiments, methods described herein can comprise: providing cellulosic biomass solids and a slurry catalyst in a hydrothermal digestion unit, the slurry catalyst being capable of activating molecular hydrogen; heating the cellulosic biomass solids in the hydrothermal digestion unit in the presence molecular hydrogen while circulating the slurry catalyst through the cellulosic biomass solids in a digestion solvent, thereby forming a liquor phase comprising soluble carbohydrates; and performing a first catalytic reduction reaction on the soluble carbohydrates within the hydrothermal digestion unit, thereby at least partially forming a reaction product comprising a triol, a diol, a monohydric alcohol, or any combination thereof in the hydrothermal digestion unit.

In some embodiments, heating the cellulosic biomass solids may take place while the hydrothermal digestion unit is in a pressurized state. As used herein, the term "pressurized state" refers to a pressure that is greater than atmospheric pressure (1 bar). Heating a digestion solvent in a pressurized state may allow the normal boiling point of the digestion solvent to be exceeded, thereby allowing the rate of hydrothermal digestion to be increased relative to lower temperature digestion processes. In some embodiments, heating the cellulosic biomass solids in the hydrothermal digestion unit may take place at a pressure of at least about 30 bar. In some embodiments, heating the cellulosic biomass solids in the hydrothermal digestion unit may take place at a pressure of at least about 60 bar or at a pressure of at least about 90 bar. In some embodiments, heating the cellulosic biomass solids in the hydrothermal digestion unit may take place at a pressure ranging between about 30 bar and about 430 bar. In some embodiments, heating the cellulosic biomass solids in the hydrothermal digestion unit may take place at a pressure ranging between about 50 bar and about 330 bar, or at a pressure ranging between about 70 bar and about 130 bar, or at a pressure ranging between about 30 bar and about 130 bar.

In some embodiments, the cellulosic biomass solids may be maintained at pressure of at least about 30 bar and heated at a temperature of at least about 150° C. In some embodiments, the cellulosic biomass solids may be maintained at a pressure of at least about 70 bar, or at least about 100 bar, and heated at a temperature of at least about 150° C. In some or other embodiments, the cellulosic biomass solids may be heated at a temperature of at least about 200° C., or at least about 250° C., or at least about 300° C.

In some embodiments, the cellulosic biomass solids and the slurry catalyst may be provided in the hydrothermal digestion unit at the same time. For example, in some embodiments, a mixture of cellulosic biomass solids and the slurry catalyst may be concurrently introduced to the hydrothermal digestion unit. In other embodiments, the cellulosic biomass solids and the slurry catalyst may be added at the same time in separate streams to the hydrothermal digestion unit. When introduced to the hydrothermal digestion unit at the same time as the cellulosic biomass solids, the slurry catalyst can either be distributed in the cellulosic biomass solids or it can remain undistributed.

In some embodiments, the cellulosic biomass solids and the slurry catalyst may be provided in the hydrothermal digestion unit separately. In some embodiments, the slurry catalyst may be provided in the hydrothermal digestion unit before the cellulosic biomass solids are provided. For example, during process startup, the slurry catalyst may be provided in the hydrothermal digestion unit before the cellulosic biomass solids are provided. In some embodiments, the slurry catalyst may be placed on or near the bottom of the hydrothermal digestion unit and a charge of cellulosic biomass solids may be placed on the slurry catalyst thereafter. Placing the slurry catalyst in the hydrothermal digestion unit prior to the cellulosic biomass solids may position the slurry catalyst such that it can be distributed in the cellulosic biomass solids using upwardly directed fluid flow. In some embodiments, the slurry catalyst may be present in the hydrothermal digestion unit, optionally along with partially digested cellulosic biomass solids, while fresh cellulosic biomass solids are being added thereto.

In some embodiments, the hydrothermal digestion unit may be charged with a fixed amount of slurry catalyst, while cellulosic biomass solids are continuously or semi-continuously fed thereto, thereby allowing hydrothermal digestion to take place in a continual manner. That is, fresh cellulosic biomass solids may be added to the hydrothermal digestion unit on a continual or an as-needed basis in order to replenish cellulosic biomass solids that have been digested to form soluble carbohydrates. In some embodiments, the cellulosic biomass solids may be continuously or semi-continuously provided to the hydrothermal digestion unit while the hydrothermal digestion unit is in a pressurized state. In some embodiments, the pressurized state may comprise a pressure of at least about 30 bar. Without the ability to introduce fresh cellulosic biomass to a pressurized hydrothermal digestion unit, depressurization and cooling of the hydrothermal digestion unit may take place during biomass addition, significantly reducing the energy- and cost-efficiency of the biomass conversion process. As used herein, the term "continuous addition" and grammatical equivalents thereof will refer to a process in which cellulosic biomass solids are added to a hydrothermal digestion unit in an uninterrupted manner without fully depressurizing the hydrothermal digestion unit. As used herein, the term "semi-continuous addition" and grammatical equivalents thereof will refer to a discontinuous, but as-needed, addition of cellulosic biomass solids to a hydrothermal digestion unit without fully depressurizing the hydrothermal digestion unit. Means through which cellulosic biomass solids may be added continuously or semi-continuously to a pressurized hydrothermal digestion unit are discussed in more detail hereinbelow.

In some embodiments, cellulosic biomass solids being continuously or semi-continuously added to the hydrothermal digestion unit may be pressurized before being added to the hydrothermal digestion unit, particularly when the hydrothermal digestion unit is in a pressurized state. Pressurization of the cellulosic biomass solids from atmospheric pressure to a pressurized state may take place in one or more pressurization zones before addition of the cellulosic biomass solids to the hydrothermal digestion unit. Suitable pressurization zones that may be used for pressurizing and introducing cellulosic biomass solids to a pressurized hydrothermal digestion unit are described in more detail in commonly owned U.S. Patent Application Publications 2013/0152457 and 2013/0152458, each filed on Dec. 20, 2011, and incorporated herein by reference in its entirety. Suitable pressurization zones described therein may include, for example, pressure vessels, pressurized screw feeders, and the like. In some embodiments, multiple pressurization zones may be connected in series to increase the pressure of the cellulosic biomass solids in a stepwise manner.

In various embodiments described herein, upwardly directed fluid flow may be used to distribute the slurry catalyst within cellulosic biomass solids. As used herein, the terms "distribute," "distribution," and variants thereof refer to a condition in which a slurry catalyst is present at all heights of a cellulosic biomass charge. No particular degree of distribution is implied by use of the term "distribute" or its variants. In some embodiments, the distribution may comprise a substantially homogeneous distribution, such that a concentration of the slurry catalyst is substantially the same at all heights of a cellulosic biomass charge. In other embodiments, the distribution may comprise a heterogeneous distribution, such that different concentrations of the slurry catalyst are present at different heights of the cellulosic biomass charge. When a heterogeneous distribution of the slurry catalyst is present, a concentration of the slurry catalyst within the cellulosic biomass solids may increase from top to bottom in some embodiments or decrease from top to bottom in other embodiments. In some embodiments, the upwardly directed fluid flow velocity may be used to modulate the type of slurry catalyst distribution obtained.

In some embodiments, the upwardly directed fluid flow may commence before heating of the cellulosic biomass solids commences. Specifically, in some embodiments, distributing the slurry catalyst may take place before forming a liquor phase comprising soluble carbohydrates. In other embodiments, heating of the cellulosic biomass solids may commence before the upwardly directed fluid flow commences. Although it is generally desirable to distribute the slurry catalyst within the cellulosic biomass solids before production of soluble carbohydrates occurs, some degree of heating prior to slurry catalyst distribution may be tolerable in some embodiments. For example, if desired, the cellulosic biomass solids may first be heated at a temperature that is not sufficient to produce and/or degrade soluble carbohydrates before commencing upwardly directed fluid flow to distribute the slurry catalyst. Reasons why one might heat the cellulosic biomass solids at a temperature below that at which soluble carbohydrates are produced may include, for example, removal of non-cellulosic materials, including catalyst poisons, from the cellulosic biomass. In addition, since the hydrothermal digestion processes described herein may take place continuously, in some embodiments, the slurry catalyst may become distributed in fresh cellulosic biomass solids being charged to the hydrothermal digestion unit while hydrothermal digestion and soluble carbohydrate formation continues in the cellulosic biomass solids already present therein.

In various embodiments, the upwardly directed fluid flow may comprise one or more upwardly directed fluid streams. In various embodiments, the one or more upwardly directed fluid streams may pass through the cellulosic biomass solids, carrying the slurry catalyst thereto, and the one or more upwardly directed fluid streams may subsequently exit the hydrothermal digestion unit. In some embodiments, the upwardly directed fluid flow may comprise one upwardly directed fluid stream. In some embodiments, the upwardly directed fluid flow may comprise two upwardly directed fluid streams, or three upwardly directed fluid streams, or four upwardly directed fluid streams, or five upwardly directed fluid streams. In some embodiments, the one or more upwardly directed fluid streams may comprise a gas stream, a liquid stream, or any combination thereof.

In some embodiments, the upwardly directed fluid stream may comprise a gas stream. For example, in some embodiments, a gas stream being used for upwardly directed fluid flow may comprise a stream of molecular hydrogen. In some or other embodiments, steam, compressed air, or an inert gas such as nitrogen, for example, may be used in place of or in addition to a stream of molecular hydrogen. Up to about 40% steam may be present in the fluid stream in various embodiments. An upwardly directed gas stream may be used to distribute the slurry catalyst within the cellulosic biomass solids when it is desired to maintain the slurry catalyst within the hydrothermal digestion unit and/or when a liquid stream alone is insufficient to distribute the slurry catalyst, for example. Specifically, when it is desired to maintain the slurry catalyst within the hydrothermal digestion unit, a gas stream may convey the slurry catalyst within the cellulosic biomass solids and then exit the hydrothermal digestion, while leaving the slurry catalyst behind at or below the liquid level in the hydrothermal digestion unit.

In some embodiments, the upwardly directed fluid stream may comprise a liquid stream. An upwardly directed liquid stream may be used to distribute the slurry catalyst within the cellulosic biomass solids when it is not desired to maintain the slurry catalyst within the hydrothermal digestion unit and/or when a gas stream alone is insufficient to distribute the slurry catalyst, for example. Unlike a gas stream, described above, a liquid stream may, in some embodiments, carry the slurry catalyst out of the digestive zone when exiting the hydrothermal digestion unit. In some embodiments, the liquid stream may comprise a stream of the digestion solvent. In some embodiments, the digestion solvent may comprise the reaction product formed in the hydrothermal digestion unit.

In some embodiments, at least a portion of the slurry catalyst may be fluidly suspended in the digestion solvent by the upwardly directed fluid flow. As used herein, the term "fluidly suspended" refers to the condition that exists when the upwardly directed fluid flow velocity matches the terminal velocity of the slurry catalyst particulates. Accordingly, fluidly suspended slurry catalyst particulates neither sink to the bottom of the hydrothermal digestion unit nor pass completely through the top of a cellulosic biomass charge, carried by the upwardly directed fluid flow. In embodiments in which the slurry catalyst is fluidly suspended, introduction of further slurry catalyst to the cellulosic biomass solids may not be needed, since the slurry catalyst is being retained therein. As described above, attaining a fluidly suspended state for the slurry catalyst may comprise sizing the slurry catalyst particulates to match an intended velocity of upwardly directed fluid flow, adjusting the velocity of upwardly directed fluid flow to match the range of particulate sizes present in a given slurry catalyst, or any combination thereof. Depending on the foregoing factors and others, all of the slurry catalyst particulates may be fluidly suspended in some embodiments, or only a portion of the slurry catalyst particulates may be fluidly suspended in other embodiments.

In some embodiments, at least a portion of the slurry catalyst may be transported through the cellulosic biomass solids by the upwardly directed fluid flow. In some embodiments, only a portion of the slurry catalyst may be transported through the cellulosic biomass solids by the upwardly directed fluid flow. In other embodiments, all of the slurry catalyst may be transported through the cellulosic biomass solids by the upwardly directed fluid flow. Slurry catalyst particulates may be transported through the cellulosic biomass solids by the upwardly directed fluid flow if the upwardly directed fluid flow velocity exceeds the terminal velocity of the slurry catalyst particulates. In such embodiments, the slurry catalyst particulates may exit the hydrothermal digestion unit with any exiting digestion solvent. When the slurry catalyst is being transported through the cellulosic biomass solids, replenishing the hydrothermal digestion unit with the slurry catalyst may be desirable. In some embodiments, fresh slurry catalyst may be provided to the hydrothermal digestion unit to replace that exiting the hydrothermal digestion unit. For example, in some embodiments, fresh slurry catalyst may be provided via a feed to the bottom of the hydrothermal digestion unit for subsequent distribution in the cellulosic biomass solids by the upwardly directed fluid flow. In some embodiments, the slurry catalyst exiting the hydrothermal digestion unit may be returned thereto and subsequently re-distributed in the cellulosic biomass solids.

In some embodiments, the slurry catalyst may be circulated though the hydrothermal digestion unit using upwardly directed fluid flow. As used herein, the term "circulate" and variants thereof will be used to refer to the condition that exists when at least a portion of a slurry catalyst is transported through the hydrothermal digestion unit more than one time. Specifically, a circulating slurry catalyst may exit the hydrothermal digestion unit and be subsequently re-introduced thereto. In some embodiments, the methods described herein may further comprise circulating the slurry catalyst external to the hydrothermal digestion unit and returning the slurry catalyst thereto. For example, in some embodiments, the slurry catalyst may circulate in a fluid conduit external to the hydrothermal digestion unit. In some embodiments, the fluid conduit may comprise a fluid circulation loop that connects an upper portion of the hydrothermal digestion unit to a lower portion of the hydrothermal digestion unit. For example, in some embodiments, the slurry catalyst may be returned to the bottom of the hydrothermal digestion unit.

As alluded to above, circulating a slurry catalyst through cellulosic biomass solids in a hydrothermal digestion unit may alleviate several difficulties associated with catalyst distribution. Foremost, circulation of the slurry catalyst eliminates the need to retain the slurry catalyst in a single location, as is often performed with slurry catalysts. In addition, by circulating the slurry catalyst, one can ensure that the entire height of a cellulosic biomass charge is exposed to the slurry catalyst. Even when the entire height of the cellulosic biomass charge is exposed to the slurry catalyst, the concentration of the slurry catalyst in the digestion solvent need not necessarily be constant. In some embodiments, the slurry catalyst may be circulated at a velocity of upward fluid flow that is sufficient to make a concentration of slurry catalyst in the liquor phase substantially homogeneous. Specifically, in such embodiments, the upward fluid flow velocity can be sufficient to fluidize all sizes of slurry catalyst particulates, such that they are all transported through the cellulosic biomass solids and exit the hydrothermal digestion unit. Under such conditions, given enough time, a substantially homogeneous distribution of the slurry catalyst in the circulating fluid phase may be obtained. In other embodiments, the velocity of the upwardly directed fluid flow may be such that a non-homogeneous concentration of the slurry catalyst particulates in the liquor phase is obtained. Specifically, in such embodiments, the velocity of upwardly directed fluid flow may be sufficient to transport and circulate a portion of the slurry catalyst particulates through the cellulosic biomass solids, while another portion of the slurry catalyst particulates remain fluidly suspended and/or non-suspended in the digestion solvent and non-circulating. Accordingly, in such embodiments, a concentration of the slurry catalyst within the cellulosic biomass solids may differ from that of the circulating slurry catalyst (e.g., external to the hydrothermal digestion unit).

Suitable hydrothermal digestion units configured for circulating a slurry catalyst therethrough are described in commonly owned U.S. Patent Application No. 61/665,717, filed Jun. 28, 2012 entitled "Digestion Units Configured for High Yield Cellulosic Biomass Processing," filed concurrently herewith and incorporated by reference in its entirety. For example, in some embodiments, the hydrothermal digestion units may comprise a fluid circulation loop that fluidly connects the upper 20% of the hydrothermal digestion unit to the lower 20% of the hydrothermal digestion unit. In some embodiments, the fluid circulation loop may fluidly connect the upper 20% of the hydrothermal digestion unit to the lower 10% of the digestion unit, or the lower 5% of the hydrothermal digestion unit, or the bottom of the hydrothermal digestion unit.

In various embodiments, the first catalytic reduction reaction performed in the hydrothermal digestion unit may take place in the presence of molecular hydrogen. In some embodiments, the molecular hydrogen may be externally supplied to the hydrothermal digestion unit. For example, in some embodiments, the molecular hydrogen may be supplied with the upwardly directed fluid flow. In some or other embodiments, the molecular hydrogen may be generated internally through use of an aqueous phase reforming (APR) catalyst. Generation of molecular hydrogen using an APR catalyst may take place within the hydrothermal digestion unit in some embodiments or externally in other embodiments.

In some embodiments, the slurry catalyst may comprise a poison-tolerant catalyst. Use of a poison-tolerant catalyst may be particularly desirable when catalyst poisons are not removed from the cellulosic biomass solids before production of soluble carbohydrates takes place. As used herein, a "poison-tolerant catalyst" is defined as a catalyst that is capable of activating molecular hydrogen without needing to be regenerated or replaced due to low catalytic activity for at least about 12 hours of continuous operation. Use of a poison-tolerant catalyst may lessen the disadvantages of process downtime that are associated with catalyst regeneration/replacement and process restart.

In some embodiments, suitable poison-tolerant catalysts may include, for example, a sulfided catalyst. In some or other embodiments, a nitrided catalyst may be used as a poison-tolerant catalyst. Sulfided catalysts suitable for activating molecular hydrogen (Sulfided Molecular Hydrogen Activating Catalysts) are described in commonly owned U.S. Patent Application Publications 2012/0317872, 2012/0317873, and 2013/0109896, each of which is incorporated herein by reference in its entirety. Sulfiding may take place by treating the catalyst with hydrogen sulfide or an alternative sulfiding agent, optionally while the catalyst is disposed on a solid support. In more particular embodiments, the poison-tolerant catalyst may comprise a sulfided cobalt-molybdate catalyst. We have found that sulfided cobalt-molybdate catalysts, depending on the reaction conditions, may produce C2-C6 monohydric alcohols, diols (including glycols), triols, and combinations thereof, while not forming an excessive amount of C2-C4 alkanes. As used herein, the term "monohydric alcohol" refers to an organic molecule containing a single alcohol functional group. Monohydric alcohols formed may be readily separated from water via flash vaporization or liquid-liquid phase separation, and undergo condensation-oligomerization reactions in separate steps over an acid or base catalyst, to produce liquid biofuels in the gasoline, jet, or diesel range. Slurry catalysts containing Pt or Pd may also be particularly useful poison-tolerant catalysts for use in the present embodiments.

In some embodiments, slurry catalysts suitable for use in the methods described herein may be sulfided by dispersing a slurry catalyst in a fluid phase and adding a sulfiding agent thereto. Suitable sulfiding agents may include, for example, organic sulfoxides (e.g., dimethyl sulfoxide), hydrogen sulfide, salts of hydrogen sulfide (e.g., NaSH), and the like. In some embodiments, the slurry catalyst may be concentrated in the fluid phase after sulfiding and then added to the hydrothermal digestion unit.

In some embodiments, the slurry catalyst may be regenerable. For example, in some embodiments, the slurry catalyst may be regenerable through exposure to water at a temperature above its normal boiling point. As used herein, a "regenerable catalyst" may have at least some of its catalytic activity restored through regeneration, even when poisoned with nitrogen compound impurities, sulfur compound impurities, or any combination thereof. Ideally, such regenerable catalysts should be regenerable with a minimal amount of process downtime. In some embodiments, the slurry catalyst may be regenerated through exposure to water having a temperature of at least about 200° C. In some embodiments, the slurry catalyst may be regenerated through exposure to water having a temperature of at least about 250° C., or at least about 300° C., or at least about 350° C., or at least about 400° C. The water used for regenerating the slurry catalyst may be in a subcritical state or a supercritical state. A particularly suitable slurry catalyst that can be regenerated though exposure to water above its normal boiling point is ruthenium disposed on a solid support such as, for example, ruthenium on titanium dioxide or ruthenium on carbon. Other suitable slurry catalysts may include a platinum or palladium compound disposed on a solid support. Most catalysts effective for mediating a catalytic reduction reaction are also regenerable, at least in part, through thermal treatments with hydrogen. Regeneration of the slurry catalyst may take place in the hydrothermal digestion unit or elsewhere, if desired.

In various embodiments, the slurry catalyst may have a particulate size of about 250 microns or less. In some embodiments, the slurry catalyst may have a particulate size of about 100 microns or less. In some embodiments, the slurry catalyst may have a particulate size of about 10 microns or less. In some embodiments, the minimum particulate size of the slurry catalyst may be about 1 micron. In some embodiments, the slurry catalyst may comprise catalyst fines in the processes described herein. As used herein, the term "catalyst fines" refers to solid catalysts having a nominal particulate size of about 100 microns or less. Catalyst fines may be generated from catalyst production processes, for example, during extrusion of solid catalyst. Catalyst fines may also be produced by grinding larger catalyst solids or during regeneration of catalyst solids. Suitable methods for producing catalyst fines are described in U.S. Pat. Nos. 6,030,915 and 6,127,299, each of which is incorporated herein by reference in its entirety. In some instances, catalyst fines may be removed from a solid catalyst production run, since they may be difficult to sequester in some catalytic processes. Techniques for removing catalyst fines from larger catalyst solids may include, for example, sieving or like size separation processes. Since there is no requirement to retain the catalyst in a fixed location in the embodiments described herein, catalyst fines may be particularly well tolerated. Advantageously, due to their small size, catalyst fines may be easily fluidized and distributed throughout the cellulosic biomass solids.

In some embodiments, the slurry catalyst may be operable to generate molecular hydrogen. For example, in some embodiments, catalysts suitable for aqueous phase reforming (i.e., APR catalysts) may be used. Suitable APR catalysts may include, for example, catalysts comprising platinum, palladium, ruthenium, nickel, cobalt, or other Group VIII metals alloyed or modified with rhenium, molybdenum, tin, or other metals. Thus, in some embodiments described herein, an external hydrogen feed may not be needed. However, in other embodiments, an external hydrogen feed may be used, optionally in combination with internally generated hydrogen.

In addition to circulating the slurry catalyst, the methods described herein may further comprise circulating cellulosic biomass fines external to the hydrothermal digestion unit in some embodiments. As described above, the formation of cellulosic biomass fines may ordinarily be problematic when performing complete or near-complete digestion of cellulosic biomass solids due to the opportunity for the cellulosic biomass fines to plug transfer lines, reactor beds, and the like. Since a slurry catalyst is already circulating in some embodiments described herein, the cellulosic biomass fines may be co-flowed with the slurry catalyst particulates, if desired. Specifically, the upwardly directed fluid flow velocity may be adjusted such that the cellulosic biomass fines also become fluidly mobile in the circulating digestion solvent.

In addition to cellulosic biomass fines, the upwardly directly fluid flow may fluidize the cellulosic biomass solids in some embodiments. In other embodiments, the upwardly directed fluid flow does not substantially fluidize the cellulosic biomass solids. One of ordinary skill in the art will be able to choose an appropriate velocity of the upwardly directed fluid flow suitable for a given application. In some embodiments, the upwardly directed fluid flow may at least partially expand the cellulosic biomass solids within the hydrothermal digestion unit. At least partial expansion of the cellulosic biomass solids may be beneficial to ensure good distribution of the slurry catalyst therein and/or to reduce the likelihood of blockages occurring in the hydrothermal digestion unit. As used herein the terms "at least partially expand" and "at least partial expansion" refer to a condition in which the packing density of the cellulosic biomass solids is reduced by the upwardly directed fluid flow.

In some instances it may be desirable to conduct further catalytic reduction reactions on the reaction product (e.g., triols, diols, and/or monohydric alcohols) produced in the hydrothermal digestion unit. For example, it may be desirable to perform further hydrogenolysis reactions to reduce the molecular weight of the reaction products, or it may be desirable to affect a further reduction in the degree of oxygenation of the reaction product. In some embodiments, the methods described herein may further comprise transferring at least a portion of the liquor phase from the hydrothermal digestion unit, and performing a second catalytic reduction reaction thereon so as to further form the reaction product. For example, in some embodiments, the reaction product formed in the hydrothermal digestion unit may be transferred from the hydrothermal digestion unit to a reactor configured for conducting a catalytic reduction reaction, where the degree of oxygenation of the reaction product may be further lowered. Specifically, in some embodiments, the second catalytic reduction reaction may be used to increase the amount of monohydric alcohols present in the reaction product. In some embodiments, at least a portion of the reaction product produced in the second catalytic reduction reaction may be recirculated to the hydrothermal digestion unit.

In other embodiments, the reaction product from the hydrothermal digestion unit may be processed directly into fuel blends without performing a second catalytic reduction reaction thereon. In such cases, it may be desirable to remove the slurry catalyst therefrom before conducting further downstream reforming reactions.

When performing a second catalytic reduction reaction, the catalyst used in the reactor may be the same or different than that used in the hydrothermal digestion unit. In some embodiments, the catalyst used for performing the second catalytic reduction reaction may be a slurry catalyst, which may be the same slurry catalyst used in the hydrothermal digestion unit or a different slurry catalyst. In other embodiments, the catalyst used for performing the second catalytic reduction reaction may be different. In some embodiments, the catalyst used for conducting the second catalytic reduction reaction may comprise a fixed bed catalyst, an ebullating bed catalyst, a fluidized bed catalyst, or the like. In embodiments in which a different catalyst is used for conducting the second catalytic reduction reaction, the slurry catalyst may be prevented from entering the reactor in which the second catalytic reduction reaction is being conducted. For example, a catalyst screen may be used in some embodiments to limit the incursion of the slurry catalyst into the reactor in which the second catalytic reduction reaction is being conducted. In other embodiments, a solids separation mechanism such one or more filters, one or more mechanical force-based separators, such as a hydroclone, or the like may be used to limit the incursion of the slurry catalyst into the reactor in which the second catalytic reduction reaction is being conducted. Like techniques may be used to remove the slurry catalyst prior to further transforming the reaction product by other downstream reforming reactions as well.

In some embodiments, one or more separation or purification steps may be employed after the liquor phase exits the hydrothermal digestion unit. Separation or purification steps that may be performed include, for example, ion-exchange, flash distillation, adsorption, and the like. Thereafter, further transformation of the reaction product may take place.

Application of the methods described herein may allow high percentages of a cellulosic biomass charge to be solubilized by digestion. In some embodiments, at least about 60% of the cellulosic biomass solids, on a dry basis, may be digested to produce a hydrolysate comprising soluble carbohydrates. In some embodiments, at least about 70% of the cellulosic biomass solids, on a dry basis, may be digested to produce a hydrolysate comprising soluble carbohydrates. In some embodiments, at least about 80% of the cellulosic biomass solids, on a dry basis, may be digested to produce a hydrolysate comprising soluble carbohydrates. In some embodiments, at least about 90% of the cellulosic biomass solids, on a dry basis, may be digested to produce a hydrolysate comprising soluble carbohydrates. In some embodiments, at least about 95% of the cellulosic biomass solids, on a dry basis, may be digested to produce a hydrolysate comprising soluble carbohydrates. In some embodiments, at least about 97% of the cellulosic biomass solids, on a dry basis, may be digested to produce a hydrolysate comprising soluble carbohydrates. In some embodiments, at least about 99% of the cellulosic biomass solids, on a dry basis, may be digested to produce a hydrolysate comprising soluble carbohydrates.

In some or other embodiments, at least about 60% of the soluble carbohydrates produced by hydrothermal digestion may form a reaction product comprising a triol, a diol, a monohydric alcohol, or any combination thereof. In some or other embodiments, at least about 70% of the soluble carbohydrates produced by hydrothermal digestion may form a reaction product comprising a triol, a diol, a monohydric alcohol, or any combination thereof. In some or other embodiments, at least about 80% of the soluble carbohydrates produced by hydrothermal digestion may form a reaction product comprising a triol, a diol, a monohydric alcohol, or any combination thereof. In some or other embodiments, at least about 90% of the soluble carbohydrates produced by hydrothermal digestion may form a reaction product comprising a triol, a diol, a monohydric alcohol, or any combination thereof. In some or other embodiments, at least about 95% of the soluble carbohydrates produced by hydrothermal digestion may form a reaction product comprising a triol, a diol, a monohydric alcohol, or any combination thereof.

In some embodiments, methods described herein may further comprise removing a solid from the reaction product. Solids removed from the reaction product may comprise the slurry catalyst, cellulosic biomass fines, or any combination thereof. Suitable solid separation mechanisms may include, for example, filters, centrifugal force- or centrifugal force-based separation mechanisms (e.g., hydroclones), settling tanks, centrifuges, and the like. Suitable filters may include, for example, surface filters and depth filters. Surface filters may include, for example, filter papers, membranes, porous solid media, and the like. Depth filters may include, for example, a column or plug of porous media designed to trap solids within its core structure. In some embodiments, two or more filters may be used, where at least one of the filters may be backflushed while forward fluid flow continues through at least some of the remaining filters. In some embodiments, one or more hydroclones may be used.

In some embodiments, prior to hydrothermal digestion, the cellulosic biomass solids may be washed, chemically treated, and/or reduced in size (e.g., by chopping, crushing, debarking, and the like) to achieve a desired size and quality for being digested. In some embodiments, the foregoing operations may remove substances that interfere with further chemical transformation of soluble carbohydrates and/or improve the penetration of the digestion solvent into the cellulosic biomass solids. In some embodiments, washing or chemical treatment of the cellulosic biomass solids may occur within the hydrothermal digestion unit before hydrothermal digestion occurs. In other embodiments, washing or chemical treatment of the cellulosic biomass solids may occur before the biomass is provided in the hydrothermal digestion unit.

In some embodiments, the present methods may further comprise performing a phase separation of the reaction product. In various embodiments, performing a phase separation may comprise separating a bilayer, conducting a solvent stripping operation, performing an extraction, performing a filtration, performing a distillation, or the like. In some embodiments, azeotropic distillation may be conducted.

In some embodiments, the methods described herein may further comprise converting the reaction product into a biofuel. As used herein, the term "biofuel" will refer to any transportation fuel formed from a biological source. Such biofuels may also be referred to herein as "fuel blends." In some embodiments, conversion of the reaction product into a biofuel may begin with a catalytic reduction reaction to transform soluble carbohydrates produced from hydrothermal digestion into a more stable reaction product, as described above. In some embodiments, the reaction product may be further transformed by any number of further catalytic reforming reactions including, for example, further catalytic reduction reactions (e.g., hydrogenolysis reactions, hydrogenation reactions, hydrotreating reactions, and the like), condensation reactions, isomerization reactions, desulfurization reactions, dehydration reactions, oligomerization reactions, alkylation reactions, and the like. A description of the initial hydrogenolysis reaction and the further catalytic reforming reactions are described hereinafter.

Various processes are known for performing hydrogenolysis of carbohydrates. One suitable method includes contacting a carbohydrate or stable hydroxyl intermediate with hydrogen, optionally mixed with a diluent gas, and a hydrogenolysis catalyst under conditions effective to form a reaction product comprising oxygenated intermediates such as, for example, smaller molecules or polyols. As used herein, the term "smaller molecules or polyols" includes any molecule that have a lower molecular weight, which may include a smaller number of carbon atoms or oxygen atoms, than the starting carbohydrate. In some embodiments, the reaction products may include smaller molecules such as, for example, polyols and alcohols. This aspect of hydrogenolysis entails the breaking of carbon-carbon bonds.

In some embodiments, a soluble carbohydrate may be converted to relatively stable oxygenated intermediates such as, for example, propylene glycol, ethylene glycol, and glycerol using a hydrogenolysis reaction in the presence of a catalyst that is capable of activating molecular hydrogen. Suitable catalysts may include, for example, Cr, Mo, W, Re, Mn, Cu, Cd, Fe, Co, Ni, Pt, Pd, Rh, Ru, Ir, Os, and alloys or any combination thereof, either alone or with promoters such as Au, Ag, Cr, Zn, Mn, Sn, Bi, B, O, and alloys or any combination thereof. In some embodiments, the catalysts and promoters may allow for hydrogenation and hydrogenolysis reactions to occur at the same time or in succession, such as the hydrogenation of a carbonyl group to form an alcohol. The catalyst may also include a carbonaceous pyropolymer catalyst containing transition metals (e.g., chromium, molybdenum, tungsten, rhenium, manganese, copper, and cadmium) or Group VIII metals (e.g., iron, cobalt, nickel, platinum, palladium, rhodium, ruthenium, iridium, and osmium). In certain embodiments, the catalyst may include any of the above metals combined with an alkaline earth metal oxide or adhered to a catalytically active support. In certain embodiments, the catalyst described in the hydrogenolysis reaction may include a catalyst support.

The conditions under which to carry out the hydrogenolysis reaction will vary based on the type of biomass starting material and the desired products (e.g. gasoline or diesel), for example. One of ordinary skill in the art, with the benefit of this disclosure, will recognize the appropriate conditions to use to carry out the reaction. In general, the hydrogenolysis reaction may be conducted at temperatures in the range of about 110° C. to about 300° C., and preferably from about 170° C. to about 300° C., and most preferably from about 180° C. to about 290° C.

In some embodiments, the hydrogenolysis reaction may be conducted under basic conditions, preferably at a pH of about 8 to about 13, and even more preferably at a pH of about 10 to about 12. In some embodiments, the hydrogenolysis reaction may be conducted at a pressure ranging between about 1 bar (absolute) and about 150 bar, and preferably at a pressure ranging between about 15 bar and about 140 bar, and even more preferably at a pressure ranging between 50 bar and 110 bar.

The hydrogen used in the hydrogenolysis reaction may include external hydrogen, recycled hydrogen, in situ generated hydrogen, or any combination thereof.

In some embodiments, the reaction products of the hydrogenolysis reaction may comprise greater than about 25% by mole, or alternatively, greater than about 30% by mole of polyols, which may result in a greater conversion to a biofuel in a subsequent processing reaction.

In some embodiments, hydrogenolysis may be conducted under neutral or acidic conditions, as needed to accelerate hydrolysis reactions in addition to the hydrogenolysis reaction. For example, hydrolysis of oligomeric carbohydrates may be combined with hydrogenation to produce sugar alcohols, which may undergo hydrogenolysis.

A second aspect of hydrogenolysis entails the breaking of —OH bonds such as: $RC(H)_2$—$OH + H_2 \rightarrow RCH_3 + H_2O$. This reaction is also called "hydrodeoxygenation," and may occur in parallel with C—C bond breaking hydrogenolysis. Diols may be converted to mono-oxygenates via this reaction. As reaction severity is increased with increased temperature or contact time with catalyst, the concentration of polyols and diols relative to mono-oxygenates may diminish as a result of hydrodeoxygenation. Selectivity for C—C vs. C—OH bond hydrogenolysis will vary with catalyst type and formulation. Full de-oxygenation to alkanes may also occur, but is generally undesirable if the intent is to produce mono-oxygenates or diols and polyols which may be condensed or oligomerized to higher molecular weight compounds in a subsequent processing step. Typically, it is desirable to send only mono-oxygenates or diols to subsequent processing steps, as higher polyols may lead to excessive coke formation during condensation or oligomerization. Alkanes, in contrast, are essentially unreactive and cannot be readily combined to produce higher molecular compounds.

Once oxygenated intermediates have been formed by a hydrogenolysis reaction, a portion of the reaction product may be recirculated to the hydrothermal digestion unit to serve as an internally generated digestion solvent. Another portion of the reaction product may be withdrawn and subsequently processed by further reforming reactions to form a biofuel. Before being subjected to the further reforming reactions, the oxygenated intermediates may optionally be separated into different components. Suitable separations may include, for example, phase separation, solvent stripping columns, extractors, filters, distillations and the like. In some embodiments, a separation of lignin from the oxygenated intermediates may be conducted before the reaction product is subsequently processed further or recirculated to the hydrothermal digestion unit.

The oxygenated intermediates may be processed to produce a fuel blend in one or more processing reactions. In some embodiments, a condensation reaction may be used along with other reactions to generate a fuel blend and may be catalyzed by a catalyst comprising an acid, a base, or both. In general, without being limited to any particular theory, it is believed that the basic condensation reactions may involve a series of steps involving: (1) an optional dehydrogenation reaction; (2) an optional dehydration reaction that may be acid catalyzed; (3) an aldol condensation reaction; (4) an optional ketonization reaction; (5) an optional furanic ring opening reaction; (6) hydrogenation of the resulting condensation products to form a >C4 hydrocarbon; and (7) any combination thereof. Acid catalyzed condensations may similarly entail optional hydrogenation or dehydrogenation reactions, dehydration, and oligomerization reactions. Additional polishing reactions may also be used to conform the product to a specific fuel standard, including reactions conducted in the presence of hydrogen and a hydrogenation catalyst to remove functional groups from final fuel product. In some embodiments, a basic catalyst, a catalyst having both an acid and a base functional site, and optionally comprising a metal function, may also be used to effect the condensation reaction.

In some embodiments, an aldol condensation reaction may be used to produce a fuel blend meeting the requirements for a diesel fuel or jet fuel. Traditional diesel fuels are petroleum distillates rich in paraffinic hydrocarbons. They have boiling ranges as broad as 187° C. to 417° C., which are suitable for combustion in a compression ignition engine, such as a diesel engine vehicle. The American Society of Testing and Materials (ASTM) establishes the grade of diesel according to the boiling range, along with allowable ranges of other fuel properties, such as cetane number, cloud point, flash point, viscosity, aniline point, sulfur content, water content, ash content, copper strip corrosion, and carbon residue. Thus, any fuel blend meeting ASTM D975 may be defined as diesel fuel.

The present disclosure also provides methods to produce jet fuel. Jet fuel is clear to straw colored. The most common fuel is an unleaded/paraffin oil-based fuel classified as Aeroplane A-1, which is produced to an internationally standardized set of specifications. Jet fuel is a mixture of a large number of different hydrocarbons, possibly as many as a thousand or more. The range of their sizes (molecular weights or carbon numbers) is restricted by the requirements for the product, for example, freezing point or smoke point. Kerosene-type Airplane fuel (including Jet A and Jet A-1) has a carbon number distribution between about C8 and C16. Wide-cut or naphtha-type Airplane fuel (including Jet B) typically has a carbon number distribution between about C5 and C15. A fuel blend meeting ASTM D1655 may be defined as jet fuel.

In certain embodiments, both Airplanes (Jet A and Jet B) contain a number of additives. Useful additives include, but are not limited to, antioxidants, antistatic agents, corrosion inhibitors, and fuel system icing inhibitor (FSII) agents. Antioxidants prevent gumming and usually, are based on alkylated phenols, for example, AO-30, AO-31, or AO-37. Antistatic agents dissipate static electricity and prevent sparking. Stadis 450 with dinonylnaphthylsulfonic acid (DINNSA) as the active ingredient, is an example. Corrosion inhibitors (e.g., DCI-4A) are used for civilian and military fuels, and DCI-6A is used for military fuels. FSII agents, include, for example, Di-EGME.

In some embodiments, the oxygenated intermediates may comprise a carbonyl-containing compound that may take part in a base catalyzed condensation reaction. In some embodiments, an optional dehydrogenation reaction may be used to increase the amount of carbonyl-containing compounds in the oxygenated intermediate stream to be used as a feed to the condensation reaction. In these embodiments, the oxygenated intermediates and/or a portion of the bio-based feedstock stream may be dehydrogenated in the presence of a catalyst.

In some embodiments, a dehydrogenation catalyst may be preferred for an oxygenated intermediate stream comprising alcohols, diols, and triols. In general, alcohols cannot participate in aldol condensation directly. The hydroxyl group or groups present may be converted into carbonyls (e.g., aldehydes, ketones, etc.) in order to participate in an aldol condensation reaction. A dehydrogenation catalyst may be included to effect dehydrogenation of any alcohols, diols, or polyols present to form ketones and aldehydes. The dehydration catalyst is typically formed from the same metals as used for hydrogenation, hydrogenolysis, or aqueous phase reforming. These catalysts are described in more detail above. Dehydrogenation yields may be enhanced by the removal or consumption of hydrogen as it forms during the reaction. The dehydrogenation step may be carried out as a separate reaction step before an aldol condensation reaction, or the dehydrogenation reaction may be carried out in concert with the aldol condensation reaction. For concerted dehydrogenation and aldol condensation reactions, the dehydrogenation and aldol condensation functions may take place on the same catalyst. For example, a metal hydrogenation/dehydrogenation functionality may be present on catalyst comprising a basic functionality.

The dehydrogenation reaction may result in the production of a carbonyl-containing compound. Suitable carbonyl-containing compounds may include, but are not limited to, any compound comprising a carbonyl functional group that may form carbanion species or may react in a condensation reaction with a carbanion species. In an embodiment, a carbonyl-containing compound may include, but is not limited to, ketones, aldehydes, furfurals, hydroxy carboxylic acids, and, carboxylic acids. Ketones may include, without limitation, hydroxyketones, cyclic ketones, diketones, acetone, propanone, 2-oxopropanal, butanone, butane-2,3-dione, 3-hydroxybutane-2-one, pentanone, cyclopentanone, pentane-2,3-dione, pentane-2,4-dione, hexanone, cyclohexanone, 2-methyl-cyclopentanone, heptanone, octanone, nonanone, decanone, undecanone, dodecanone, methylglyoxal, butanedione, pentanedione, diketohexane, dihydroxyacetone, and isomers thereof. Aldehydes may include, without limitation, hydroxyaldehydes, acetaldehyde, glyceraldehyde, propionaldehyde, butyraldehyde, pentanal, hexanal, heptanal, octanal, nonal, decanal, undecanal, dodecanal, and isomers thereof. Carboxylic acids may include, without limitation, formic acid, acetic acid, propionic acid, butanoic acid, pentanoic acid, hexanoic acid, heptanoic acid, isomers and derivatives thereof, including hydroxylated derivatives, such as 2-hydroxybutanoic acid and lactic acid. Furfurals may include, without limitation, hydroxylmethyl-furfural, 5-hydroxymethyl-2(5H)-furanone, dihydro-5-(hydroxymethyl)-2(3H)-furanone, tetrahydro-2-furoic acid, dihydro-5-(hydroxymethyl)-2(3H)-furanone, tetrahydrofurfuryl alcohol, 1-(2-furyl)ethanol, hydroxymethyltetrahydrofurfural, and isomers thereof. In an embodiment, the dehydrogenation reaction may result in the production of a carbonyl-containing compound that is combined with the oxygenated intermediates to become a part of the oxygenated intermediates fed to the condensation reaction.

In an embodiment, an acid catalyst may be used to optionally dehydrate at least a portion of the oxygenated intermediate stream. Suitable acid catalysts for use in the dehydration reaction may include, but are not limited to, mineral acids (e.g., HCl, $H_2SO_4$), solid acids (e.g., zeolites, ion-exchange resins) and acid salts (e.g., $LaCl_3$). Additional acid catalysts may include, without limitation, zeolites, carbides, nitrides, zirconia, alumina, silica, aluminosilicates, phosphates, titanium oxides, zinc oxides, vanadium oxides, lanthanum oxides, yttrium oxides, scandium oxides, magnesium oxides, cerium oxides, barium oxides, calcium oxides, hydroxides, heteropolyacids, inorganic acids, acid modified resins, base modified resins, and any combination thereof. In some embodiments, the dehydration catalyst may also include a modifier. Suitable modifiers may include, for example, La, Y, Sc, P, B, Bi, Li, Na, K, Rb, Cs, Mg, Ca, Sr, Ba, and any combination thereof. The modifiers may be useful, inter alia, to carry out a concerted hydrogenation/dehydrogenation reaction with the dehydration reaction. In some embodiments, the dehydration catalyst may also include a metal. Suitable metals may include, for example, Cu, Ag, Au, Pt, Ni, Fe, Co, Ru, Zn, Cd, Ga, In, Rh, Pd, Ir, Re, Mn, Cr, Mo, W, Sn, Os, alloys, and any combination thereof. The dehydration catalyst may be self supporting, supported on an inert support or resin, or it may be dissolved in solution.

In some embodiments, the dehydration reaction may occur in the vapor phase. In other embodiments, the dehydration reaction may occur in the liquid phase. For liquid phase dehydration reactions, an aqueous solution may be used to carry out the reaction. In an embodiment, other solvents in addition to water, may be used to form the aqueous solution. For example, water soluble organic solvents may be present. Suitable solvents may include, but are not limited to, hydroxymethylfurfural (HMF), dimethylsulfoxide (DMSO), 1-methyl-n-pyrollidone (NMP), and any combination thereof. Other suitable aprotic solvents may also be used alone or in combination with any of these solvents.

In an embodiment, the processing reactions may comprise an optional ketonization reaction. A ketonization reaction may increase the number of ketone functional groups within at least a portion of the oxygenated intermediates. For example, an alcohol may be converted into a ketone in a ketonization reaction. Ketonization may be carried out in the presence of a basic catalyst. Any of the basic catalysts described above as the basic component of the aldol condensation reaction may be used to effect a ketonization reaction. Suitable reaction conditions are known to one of ordinary skill in the art and generally correspond to the reaction conditions listed above with respect to the aldol condensation reaction. The ketonization reaction may be carried out as a separate reaction step, or it may be carried out in concert with the aldol condensation reaction. The inclusion of a basic functional site on the aldol condensation catalyst may result in concerted ketonization and aldol condensation reactions.

In some embodiments, the processing reactions may comprise an optional furanic ring opening reaction. A furanic ring opening reaction may result in the conversion of at least a portion of any oxygenated intermediates comprising a furanic ring into compounds that are more reactive in an aldol condensation reaction. A furanic ring opening reaction may be carried out in the presence of an acidic catalyst. Any of the acid catalysts described above as the acid component of the aldol condensation reaction may be used to effect a furanic ring opening reaction. Suitable reaction conditions are known to one of ordinary skill in the art and generally correspond to the reaction conditions listed above with respect to the aldol condensation reaction. The furanic ring opening reaction may be carried out as a separate reaction step, or it may be carried out in concert with the aldol condensation reaction. The inclusion of an acid functional site on the aldol condensation catalyst may result in a concerted furanic ring opening reaction and aldol condensation reactions. Such an embodiment may be advantageous as any furanic rings may be opened in the presence of an acid functionality and reacted in an aldol condensation reaction using a basic functionality. Such a concerted reaction scheme may allow for the production of a greater amount of higher hydrocarbons to be formed for a given oxygenated intermediate feed.

In some embodiments, production of a >C4 compound may occur by condensation, which may include aldol condensation of the oxygenated intermediates in the presence of a condensation catalyst. Aldol-condensation generally involves the carbon-carbon coupling between two compounds, at least one of which may contain a carbonyl group, to form a larger organic molecule. For example, acetone may react with hydroxymethylfurfural to form a C9 species, which may subsequently react with another hydroxymethylfurfural molecule to form a C15 species. In various embodiments, the reaction is usually carried out in the presence of a condensation catalyst. The condensation reaction may be carried out in the vapor or liquid phase. In an embodiment, the reaction may take place at a temperature ranging from about 5° C. to about 375° C. depending on the reactivity of the carbonyl group.

The condensation catalyst will generally be a catalyst capable of forming longer chain compounds by linking two molecules through a new carbon-carbon bond, such as a basic catalyst, a mufti-functional catalyst having both acid and base functionalities, or either type of catalyst also comprising an optional metal functionality. In some embodiments, the mufti-functional catalyst may be a catalyst having both strong acid and strong base functionalities. In some embodiments, aldol catalysts may comprise Li, Na, K, Cs, B, Rb, Mg, Ca, Sr, Si, Ba, Al, Zn, Ce, La, Y, Sc, Y, Zr, Ti, hydrotalcite, zinc-aluminate, phosphate, base-treated aluminosilicate zeolite, a basic resin, basic nitride, alloys or any combination thereof. In some embodiments, the base catalyst may also comprise an oxide of Ti, Zr, V, Nb, Ta, Mo, Cr, W, Mn, Re, Al, Ga, In, Co, Ni, Si, Cu, Zn, Sn, Cd, Mg, P, Fe, or any combination thereof. In some embodiments, the condensation catalyst comprises mixed-oxide base catalysts. Suitable mixed-oxide base catalysts may comprise a combination of magnesium, zirconium, and oxygen, which may comprise, without limitation: Si—Mg—O, Mg—Ti—O, Y—Mg—O, Y—Zr—O, Ti—Zr—O, Ce—Zr—O, Ce—Mg—O, Ca—Zr—O, La—Zr—O, B—Zr—O, La—Ti—O, B—Ti—O, and any combination thereof. Different atomic ratios of Mg/Zr or the combinations of various other elements constituting the mixed oxide catalyst may be used ranging from about 0.01 to about 50. In some embodiments, the condensation catalyst may further include a metal or alloys comprising metals, such as Cu, Ag, Au, Pt, Ni, Fe, Co, Ru, Zn, Cd, Ga, In, Rh, Pd, Ir, Re, Mn, Cr, Mo, W, Sn, Bi, Pb, Os, alloys and combinations thereof. Such metals may be preferred when a dehydrogenation reaction is to be carried out in concert with the aldol condensation reaction. In some embodiments, preferred Group IA materials may include Li, Na, K, Cs and Rb. In some embodiments, preferred Group IIA materials may include Mg, Ca, Sr and Ba. In some embodiments, Group IIB materials may include Zn and Cd. In some embodiments, Group IIIB materials may include Y and La. Basic resins may include resins that exhibit basic functionality. The basic catalyst may be self-supporting or adhered to any one of the supports further described below, including supports containing carbon, silica, alumina, zirconia, titania, vanadia, ceria, nitride, boron nitride, heteropolyacids, alloys and mixtures thereof.

In one embodiment, the condensation catalyst may be derived from the combination of MgO and $Al_2O_3$ to form a hydrotalcite material. Another preferred material contains ZnO and $Al_2O_3$ in the form of a zinc aluminate spinel. Yet another preferred material is a combination of ZnO, $Al_2O_3$, and CuO. Each of these materials may also contain an additional metal function provided by a Group VIIIB metal, such as Pd or Pt. Such metals may be preferred when a dehydrogenation reaction is to be carried out in concert with the aldol condensation reaction. In some embodiments, the basic catalyst may be a metal oxide containing Cu, Ni, Zn, V, Zr, or mixtures thereof. In other embodiments, the basic catalyst may be a zinc aluminate metal containing Pt, Pd Cu, Ni, or mixtures thereof.

In some embodiments, a base-catalyzed condensation reaction may be performed using a condensation catalyst with both an acidic and a basic functionality. The acid-aldol condensation catalyst may comprise hydrotalcite, zinc-aluminate, phosphate, Li, Na, K, Cs, B, Rb, Mg, Si, Ca, Sr, Ba, Al, Ce, La, Sc, Y, Zr, Ti, Zn, Cr, or any combination thereof. In further embodiments, the acid-base catalyst may also include one or more oxides from the group of Ti, Zr, V, Nb, Ta, Mo, Cr, W, Mn, Re, Al, Ga, In, Fe, Co, Ir, Ni, Si, Cu, Zn, Sn, Cd, P, and combinations thereof. In some embodiments, the acid-base catalyst may include a metal functionality provided by Cu, Ag, Au, Pt, Ni, Fe, Co, Ru, Zn, Cd, Ga, In, Rh, Pd, Ir, Re, Mn, Cr, Mo, W, Sn, Os, alloys or combinations thereof. In some embodiments, the catalyst may further include Zn, Cd or phosphate. In some embodiments, the condensation catalyst may be a metal oxide containing Pd, Pt, Cu or Ni, and even more preferably an aluminate or zirconium metal oxide containing Mg and Cu, Pt, Pd or Ni. The acid-base catalyst may also include a hydroxyapatite (HAP) combined with any one or more of the above metals. The acid-base catalyst may be self-supporting or adhered to any one of the supports further described below, including supports containing carbon, silica, alumina, zirconia, titania, vanadia, ceria, nitride, boron nitride, heteropolyacids, alloys and mixtures thereof.

In some embodiments, the condensation catalyst may also include zeolites and other microporous supports that contain Group IA compounds, such as Li, Na, K, Cs and Rb. Preferably, the Group IA material may be present in an amount less than that required to neutralize the acidic nature of the support. A metal function may also be provided by the addition of group VIIIB metals, or Cu, Ga, In, Zn or Sn. In one embodiment, the condensation catalyst may be derived from the combination of MgO and $Al_2O_3$ to form a hydrotalcite material. Another preferred material may contain a combination of MgO and $ZrO_2$, or a combination of ZnO and $Al_2O_3$. Each of these materials may also contain an additional metal function provided by copper or a Group VIIIB metal, such as Ni, Pd, Pt, or combinations of the foregoing.

The condensation catalyst may be self-supporting (i.e., the catalyst does not need another material to serve as a support), or may require a separate support suitable for suspending the catalyst in the reactant stream. One exemplary support is silica, especially silica having a high surface area (greater than 100 square meters per gram), obtained by sol-gel synthesis, precipitation, or fuming. In other embodiments, particularly when the condensation catalyst is a powder, the catalyst system may include a binder to assist in forming the catalyst into a desirable catalyst shape. Applicable forming processes may include extrusion, pelletization, oil dropping, or other known processes. Zinc oxide, alumina, and a peptizing agent may also be mixed together and extruded to produce a formed material. After drying, this material may be calcined at a temperature appropriate for formation of the catalytically active phase. Other catalyst supports as known to one having ordinary skill in the art may also be used.

In some embodiments, a dehydration catalyst, a dehydrogenation catalyst, and the condensation catalyst may be present in the same reactor as the reaction conditions overlap to some degree. In these embodiments, a dehydration reaction and/or a dehydrogenation reaction may occur substantially simultaneously with the condensation reaction. In some embodiments, a catalyst may comprise active sites for a dehydration reaction and/or a dehydrogenation reaction in addition to a condensation reaction. For example, a catalyst may comprise active metals for a dehydration reaction and/or a dehydrogenation reaction along with a condensation reaction at separate sites on the catalyst or as alloys. Suitable active elements may comprise any of those listed above with respect to the dehydration catalyst, dehydrogenation catalyst, and the condensation catalyst. Alternately, a physical mixture of dehydration, dehydrogenation, and condensation catalysts may be employed. While not intending to be limited by theory, it is believed that using a condensation catalyst comprising a metal and/or an acid functionality may assist in pushing the equilibrium limited aldol condensation reaction toward completion. Advantageously, this may be used to effect multiple condensation reactions with dehydration and/or dehydrogenation of intermediates, in order to form (via condensation, dehydration, and/or dehydrogenation) higher molecular weight oligomers as desired to produce jet or diesel fuel.

The specific >C4 compounds produced in the condensation reaction may depend on various factors, including, without limitation, the type of oxygenated intermediates in the reactant stream, condensation temperature, condensation pressure, the reactivity of the catalyst, and the flow rate of the reactant stream. In general, the condensation reaction may be carried out at a temperature at which the thermodynamics of the proposed reaction are favorable. For condensed phase liquid reactions, the pressure within the reactor may be sufficient to maintain at least a portion of the reactants in the condensed liquid phase at the reactor inlet. For vapor phase reactions, the reaction may be carried out at a temperature where the vapor pressure of the oxygenates is at least about 0.1 bar, and the thermodynamics of the reaction are favorable. The condensation temperature will vary depending upon the specific oxygenated intermediates used, but may generally range between about 75° C. and about 500° C. for reactions taking place in the vapor phase, and more preferably range between about 125° C. and about 450° C. For liquid phase reactions, the condensation temperature may range between about 5° C. and about 475° C., and the condensation pressure may range between about 0.01 bar and about 100 bar. Preferably, the condensation temperature may range between about 15° C. and about 300° C., or between about 15° C. and 250° C.

Varying the factors above, as well as others, will generally result in a modification to the specific composition and yields of the >C4 compounds. For example, varying the temperature and/or pressure of the reactor system, or the particular catalyst formulations, may result in the production of >C4 alcohols and/or ketones instead of >C4 hydrocarbons. The >C4 hydrocarbon product may also contain a variety of olefins, and alkanes of various sizes (typically branched alkanes). Depending upon the condensation catalyst used, the hydrocarbon product may also include aromatic and cyclic hydrocarbon compounds. The >C4 hydrocarbon product may also contain undesirably high levels of olefins, which may lead to coking or deposits in combustion engines, or other undesirable hydrocarbon products. In such cases, the hydrocarbons may optionally be hydrogenated to reduce the ketones to alcohols and hydrocarbons, while the alcohols and olefinic hydrocarbons may be reduced to alkanes, thereby forming a more desirable hydrocarbon product having reduced levels of olefins, aromatics or alcohols.

The condensation reactions may be carried out in any reactor of suitable design, including continuous-flow, batch, semi-batch or multi-system reactors, without limitation as to design, size, geometry, flow rates, and the like. The reactor system may also use a fluidized catalytic bed system, a swing bed system, fixed bed system, a moving bed system, or a combination of the above. In some embodiments, bi-phasic (e.g., liquid-liquid) and tri-phasic (e.g., liquid-liquid-solid) reactors may be used to carry out the condensation reactions.

In a continuous flow system, the reactor system may include an optional dehydrogenation bed adapted to produce dehydrogenated oxygenated intermediates, an optional dehydration bed adapted to produce dehydrated oxygenated intermediates, and a condensation bed adapted to produce >C4 compounds from the oxygenated intermediates. The dehydrogenation bed may be configured to receive the reactant stream and produce the desired oxygenated intermediates, which may have an increase in the amount of carbonyl-containing compounds. The dehydration bed may be configured to receive the reactant stream and produce the desired oxygenated intermediates. The condensation bed may be configured to receive the oxygenated intermediates for contact with the condensation catalyst and production of the desired >C4 compounds. For systems with one or more finishing steps, an additional reaction bed for conducting the finishing process or processes may be included after the condensation bed.

In some embodiments, the optional dehydration reaction, the optional dehydrogenation reaction, the optional ketonization reaction, the optional ring opening reaction, and the condensation reaction catalyst beds may be positioned within the same reactor vessel or in separate reactor vessels in fluid communication with each other. Each reactor vessel preferably may include an outlet adapted to remove the product stream from the reactor vessel. For systems with one or more finishing steps, the finishing reaction bed or beds may be within the same reactor vessel along with the condensation bed or in a separate reactor vessel in fluid communication with the reactor vessel having the condensation bed.

In some embodiments, the reactor system also may include additional outlets to allow for the removal of portions of the reactant stream to further advance or direct the reaction to the desired reaction products, and to allow for the collection and recycling of reaction byproducts for use in other portions of the system. In some embodiments, the reactor system also may include additional inlets to allow for the introduction of supplemental materials to further advance or direct the reaction to the desired reaction products, and to allow for the recycling of reaction byproducts for use in other reactions.

In some embodiments, the reactor system also may include elements which allow for the separation of the reactant stream into different components which may find use in different reaction schemes or to simply promote the desired reactions. For instance, a separator unit, such as a phase separator, extractor, purifier or distillation column, may be installed prior to the condensation step to remove water from the reactant stream for purposes of advancing the condensation reaction to favor the production of higher hydrocarbons. In some embodiments, a separation unit may be installed to remove specific intermediates to allow for the production of a desired product stream containing hydrocarbons within a particular carbon number range, or for use as end products or in other systems or processes. The condensation reaction may produce a broad range of compounds with carbon numbers ranging from C4 to C30 or greater. Exemplary compounds may include, for example, >C4 alkanes, >C4 alkenes, >C5 cycloalkanes, >C5 cycloalkenes, aryls, fused aryls, >C4 alcohols, >C4 ketones, and mixtures thereof. The >C4 alkanes and >C4 alkenes may range from 4 to about 30 carbon atoms (i.e. C4-C30 alkanes and C4-C30 alkenes) and may be branched or straight chain alkanes or alkenes. The >C4 alkanes and >C4 alkenes may also include fractions of C7-C14, C12-C24 alkanes and alkenes, respectively, with the C7-C14 fraction directed to jet fuel blends, and the C12-C24 fraction directed to diesel fuel blends and other industrial applications. Examples of various >C4 alkanes and >C4 alkenes may include, without limitation, butane, butene, pentane, pentene, 2-methylbutane, hexane, hexene, 2-methylpentane, 3-methylpentane, 2,2-dimethylbutane, 2,3-dimethylbutane, heptane, heptene, octane, octene, 2,2,4,-trimethylpentane, 2,3-dimethyl hexane, 2,3,4-trimethylpentane, 2,3-dimethylpentane, nonane, nonene, decane, decene, undecane, undecene, dodecane, dodecene, tridecane, tridecene, tetradecane, tetradecene, pentadecane, pentadecene, hexadecane, hexadecene, heptyldecane, heptyldecene, octyldecane, octyldecene, nonyldecane, nonyldecene, eicosane, eicosene, uneicosane, uneicosane, doeicosane, doeicosene, trieicosane, trieicosene, tetraeicosane, tetraeicosene, and isomers thereof.

The >C5 cycloalkanes and >C5 cycloalkenes may have from 5 to about 30 carbon atoms and may be unsubstituted, mono-substituted or mufti-substituted. In the case of mono-substituted and mufti-substituted compounds, the substituted group may include a branched >C3 alkyl, a straight chain >C1 alkyl, a branched >C3 alkylene, a straight chain >C1 alkylene, a straight chain >C2 alkylene, an aryl group, or a combination thereof. In one embodiment, at least one of the substituted groups may include a branched C3-C12 alkyl, a straight chain C1-C12 alkyl, a branched C3-C12 alkylene, a straight chain C1-C12 alkylene, a straight chain C2-C12 alkylene, an aryl group, or a combination thereof. In yet other embodiments, at least one of the substituted groups may include a branched C3-C4 alkyl, a straight chain C1-C4 alkyl, a branched C3-C4 alkylene, a straight chain C1-C4 alkylene, a straight chain C2-C4 alkylene, an aryl group, or any combination thereof. Examples of desirable >C5 cycloalkanes and >C5 cycloalkenes may include, without limitation, cyclopentane, cyclopentene, cyclohexane, cyclohexene, methylcyclopentane, methylcyclopentene, ethylcyclopentane, ethylcyclopentene, ethylcyclohexane, ethylcyclohexene, and isomers thereof.

Aryl groups contain an aromatic hydrocarbon in either an unsubstituted (phenyl), mono-substituted or mufti-substituted form. In the case of mono-substituted and mufti-substituted compounds, the substituted group may include a branched >C3 alkyl, a straight chain >C1 alkyl, a branched >C3 alkylene, a straight chain >C2 alkylene, a phenyl group, or a combination thereof. In some embodiments, at least one of the substituted groups may include a branched C3-C12 alkyl, a straight chain C1-C12 alkyl, a branched C3-C12 alkylene, a straight chain C2-C12 alkylene, a phenyl group, or any combination thereof. In yet other embodiments, at least one of the substituted groups may include a branched C3-C4 alkyl, a straight chain C1-C4 alkyl, a branched C3-C4 alkylene, a straight chain C2-C4 alkylene, a phenyl group, or any combination thereof. Examples of various aryl compounds may include, without limitation, benzene, toluene, xylene (dimethylbenzene), ethyl benzene, para-xylene, meta-xylene, ortho-xylene, and C9 aromatics.

Fused aryls contain bicyclic and polycyclic aromatic hydrocarbons, in either an unsubstituted, mono-substituted or mufti-substituted form. In the case of mono-substituted and multi-substituted compounds, the substituted group may include a branched >C3 alkyl, a straight chain >C1 alkyl, a branched >C3 alkylene, a straight chain >C2 alkylene, a phenyl group, or a combination thereof. In other embodiments, at least one of the substituted groups may include a branched C3-C4 alkyl, a straight chain C1-C4 alkyl, a branched C3-C4 alkylene, a straight chain C2-C4 alkylene, a phenyl group, or any combination thereof. Examples of various fused aryls may include, without limitation, naphthalene, anthracene, tetrahydronaphthalene, and decahydronaphthalene, indane, indene, and isomers thereof.

The moderate fractions, such as C7-C14, may be separated for jet fuel, while heavier fractions, such as C12-C24, may be separated for diesel use. The heaviest fractions may be used as lubricants or cracked to produce additional gasoline and/or diesel fractions. The >C4 compounds may also find use as industrial chemicals, whether as an intermediate or an end product. For example, the aryls toluene, xylene, ethylbenzene, para-xylene, meta-xylene, and ortho-xylene may find use as chemical intermediates for the production of plastics and other products. Meanwhile, C9 aromatics and fused aryls, such as naphthalene, anthracene, tetrahydronaphthalene, and decahydronaphthalene, may find use as solvents in industrial processes.

In some embodiments, additional processes may be used to treat the fuel blend to remove certain components or further conform the fuel blend to a diesel or jet fuel standard. Suitable techniques may include hydrotreating to reduce the amount of or remove any remaining oxygen, sulfur, or nitrogen in the fuel blend. The conditions for hydrotreating a hydrocarbon stream will be known to one of ordinary skill in the art.

In some embodiments, hydrogenation may be carried out in place of or after the hydrotreating process to saturate at least some olefinic bonds. In some embodiments, a hydrogenation reaction may be carried out in concert with the aldol condensation reaction by including a metal functional group with the aldol condensation catalyst. Such hydrogenation may be performed to conform the fuel blend to a specific fuel standard (e.g., a diesel fuel standard or a jet fuel standard). The hydrogenation of the fuel blend stream may be carried out according to known procedures, either with the continuous or batch method. The hydrogenation reaction may be used to remove remaining carbonyl groups and/or hydroxyl groups. In such cases, any of the hydrogenation catalysts described above may be used. In general, the finishing step may be carried out at finishing temperatures ranging between about 80° C. and about 250° C., and finishing pressures may range between about 5 bar and about 150 bar. In some embodiments, the finishing step may be conducted in the vapor phase or liquid phase, and use, external hydrogen, recycled hydrogen, or combinations thereof, as necessary.

In some embodiments, isomerization may be used to treat the fuel blend to introduce a desired degree of branching or other shape selectivity to at least some components in the fuel blend. It may also be useful to remove any impurities before the hydrocarbons are contacted with the isomerization catalyst. The isomerization step may comprise an optional stripping step, wherein the fuel blend from the oligomerization reaction may be purified by stripping with water vapor or a suitable gas such as light hydrocarbon, nitrogen or hydrogen. The optional stripping step may be carried out in a countercurrent manner in a unit upstream of the isomerization catalyst, wherein the gas and liquid are contacted with each other, or before the actual isomerization reactor in a separate stripping unit utilizing countercurrent principle.

After the optional stripping step the fuel blend may be passed to a reactive isomerization unit comprising one or more catalyst beds. The catalyst beds of the isomerization unit may operate either in co-current or countercurrent manner. In the isomerization unit, the pressure may vary between about 20 bar to about 150 bar, preferably between about 20 bar to about 100 bar, the temperature ranging between about 195° C. and about 500° C., preferably between about 300° C. and about 400° C. In the isomerization unit, any isomerization catalyst known in the art may be used. In some embodiments, suitable isomerization catalysts may contain molecular sieve and/or a metal from Group VII and/or a carrier. In some embodiments, the isomerization catalyst may contain SAPO-11 or SAPO41 or ZSM-22 or ZSM-23 or ferrierite and Pt, Pd or Ni and $Al_2O_3$ or $SiO_2$. Typical isomerization catalysts may include, for example, Pt/SAPO-11/$Al_2O_3$, Pt/ZSM-22/$Al_2O_3$, Pt/ZSM-23/$Al_2O_3$ and Pt/SAPO-11/$SiO_2$.

Other factors, such as the concentration of water or undesired oxygenated intermediates, may also effect the composition and yields of the >C4 compounds, as well as the activity and stability of the condensation catalyst. In such cases, the process may include a dewatering step that removes a portion of the water prior to the condensation reaction and/or the optional dehydration reaction, or a separation unit for removal of the undesired oxygenated intermediates. For instance, a separator unit, such as a phase separator, extractor, purifier or distillation column, may be installed prior to the condensation reactor so as to remove a portion of the water from the reactant stream containing the oxygenated intermediates. A separation unit may also be installed to remove specific oxygenated intermediates to allow for the production of a desired product stream containing hydrocarbons within a particular carbon range, or for use as end products or in other systems or processes.

Thus, in some embodiments, the fuel blend produced by the processes described herein may be a hydrocarbon mixture that meets the requirements for jet fuel (e.g., conforms with ASTM D1655). In other embodiments, the product of the processes described herein may be a hydrocarbon mixture that comprises a fuel blend meeting the requirements for a diesel fuel (e.g., conforms with ASTM D975).

In other embodiments, a fuel blend comprising gasoline hydrocarbons (i.e., a gasoline fuel) may be produced. "Gasoline hydrocarbons" refer to hydrocarbons predominantly comprising C5-9 hydrocarbons, for example, C6-8 hydrocarbons, and having a boiling point range from 32° C. (90° F.) to about 204° C. (400° F.). Gasoline hydrocarbons may include, but are not limited to, straight run gasoline, naphtha, fluidized or thermally catalytically cracked gasoline, VB gasoline, and coker gasoline. Gasoline hydrocarbons content is determined by ASTM Method D2887.

In yet other embodiments, the >C2 olefins may be produced by catalytically reacting the oxygenated intermediates in the presence of a dehydration catalyst at a dehydration temperature and dehydration pressure to produce a reaction stream comprising the >C2 olefins. The >C2 olefins may comprise straight or branched hydrocarbons containing one or more carbon-carbon double bonds. In general, the >C2 olefins may contain from 2 to 8 carbon atoms, and more preferably from 3 to 5 carbon atoms. In some embodiments, the olefins may comprise propylene, butylene, pentylene, isomers of the foregoing, and mixtures of any two or more of the foregoing. In other embodiments, the >C2 olefins may include >C4 olefins produced by catalytically reacting a portion of the >C2 olefins over an olefin isomerization catalyst.

The dehydration catalyst may comprise a member selected from the group consisting of an acidic alumina, aluminum phosphate, silica-alumina phosphate, amorphous silica-alumina, aluminosilicate, zirconia, sulfated zirconia, tungstated zirconia, tungsten carbide, molybdenum carbide, titania, sulfated carbon, phosphated carbon, phosphated silica, phosphated alumina, acidic resin, heteropolyacid, inorganic acid, and a combination of any two or more of the foregoing. In some embodiments, the dehydration catalyst may further comprise a modifier selected from the group consisting of Ce, Y, Sc, La, Li, Na, K, Rb, Cs, Mg, Ca, Sr, Ba, P, B, Bi, and a combination of any two or more of the foregoing. In other embodiments, the dehydration catalyst may further comprise an oxide of an element, the element selected from the group consisting of Ti, Zr, V, Nb, Ta, Mo, Cr, W, Mn, Re, Al, Ga, In, Fe, Co, Ir, Ni, Si, Cu, Zn, Sn, Cd, P, and a combination of any two or more of the foregoing. In yet other embodiments, the dehydration catalyst may further comprise a metal selected from the group consisting of Cu, Ag, Au, Pt, Ni, Fe, Co, Ru, Zn, Cd, Ga, In, Rh, Pd, Ir, Re, Mn, Cr, Mo, W, Sn, Os, an alloy of any two or more of the foregoing, and a combination of any two or more of the foregoing.

In yet other embodiments, the dehydration catalyst may comprise an aluminosilicate zeolite. In some embodiments, the dehydration catalyst may further comprise a modifier selected from the group consisting of Ga, In, Zn, Fe, Mo, Ag, Au, Ni, P, Sc, Y, Ta, a lanthanide, and a combination of any two or more of the foregoing. In some embodiments, the dehydration catalyst may further comprise a metal selected from the group consisting of Cu, Ag, Au, Pt, Ni, Fe, Co, Ru, Zn, Cd, Ga, In, Rh, Pd, Ir, Re, Mn, Cr, Mo, W, Sn, Os, an alloy of any two or more of the foregoing, and a combination of any two or more of the foregoing.

In other embodiments, the dehydration catalyst may comprise a bifunctional pentasil ring-containing aluminosilicate zeolite. In some embodiments, the dehydration catalyst may further comprise a modifier selected from the group consisting of Ga, In, Zn, Fe, Mo, Ag, Au, Ni, P, Sc, Y, Ta, a lanthanide, and a combination of any two or more of the foregoing. In some embodiments, the dehydration catalyst may further comprise a metal selected from the group consisting of Cu, Ag, Au, Pt, Ni, Fe, Co, Ru, Zn, Cd, Ga, In, Rh, Pd, Ir, Re, Mn, Cr, Mo, W, Sn, Os, an alloy of any two or more of the foregoing, and a combination of any two or more of the foregoing.

The dehydration reaction may be conducted at a temperature and pressure where the thermodynamics are favorable. In general, the reaction may be performed in the vapor phase, liquid phase, or a combination of both. In some embodiments, the dehydration temperature may range between about 100° C. and about 500° C., and the dehydration pressure may range between about 1 bar (absolute) and about 60 bar. In some embodiments, the dehydration temperature may range between about 125° C. and about 450° C. In some embodiments, the dehydration temperature may range between about 150° C. and about 350° C., and the dehydration pressure may range between about 5 bar and about 50 bar. In some embodiments, the dehydration temperature may range between about 175° C. and about 325° C.

The >C6 paraffins may be produced by catalytically reacting >C2 olefins with a stream of >C4 isoparaffins in the presence of an alkylation catalyst at an alkylation temperature and alkylation pressure to produce a product stream comprising >C6 paraffins. The >C4 isoparaffins may include alkanes and cycloalkanes having 4 to 7 carbon atoms, such as isobutane, isopentane, naphthenes, and higher homologues having a tertiary carbon atom (e.g., 2-methylbutane and 2,4-dimethylpentane), isomers of the foregoing, and mixtures of any two or more of the foregoing. In some embodiments, the stream of >C4 isoparaffins may comprise internally generated >C4 isoparaffins, external >C4 isoparaffins, recycled >C4 isoparaffins, or combinations of any two or more of the foregoing.

The >C6 paraffins may be branched paraffins, but may also include normal paraffins. In one version, the >C6 paraffins may comprise a member selected from the group consisting of a branched C6-10 alkane, a branched C6 alkane, a branched C7 alkane, a branched C8 alkane, a branched C9 alkane, a branched C10 alkane, or a mixture of any two or more of the foregoing. In one version, the >C6 paraffins may include, for example, dimethylbutane, 2,2-dimethylbutane, 2,3-dimethylbutane, methylpentane, 2-methylpentane, 3-methylpentane, dimethylpentane, 2,3-dimethylpentane, 2,4-dimethylpentane, methylhexane, 2,3-dimethylhexane, 2,3,4-trimethylpentane, 2,2,4-trimethylpentane, 2,2,3-trimethylpentane, 2,3,3-trimethylpentane, dimethylhexane, or mixtures of any two or more of the foregoing.

The alkylation catalyst may comprise a member selected from the group of sulfuric acid, hydrofluoric acid, aluminum chloride, boron trifluoride, solid phosphoric acid, chlorided alumina, acidic alumina, aluminum phosphate, silica-alumina phosphate, amorphous silica-alumina, aluminosilicate, aluminosilicate zeolite, zirconia, sulfated zirconia, tungstated zirconia, tungsten carbide, molybdenum carbide, titania, sulfated carbon, phosphated carbon, phosphated silica, phosphated alumina, acidic resin, heteropolyacid, inorganic acid, and a combination of any two or more of the foregoing. The alkylation catalyst may also include a mixture of a mineral acid with a Friedel-Crafts metal halide, such as aluminum bromide, and other proton donors.

In some embodiments, the alkylation catalyst may comprise an aluminosilicate zeolite. In some embodiments, the alkylation catalyst may further comprise a modifier selected from the group consisting of Ga, In, Zn, Fe, Mo, Ag, Au, Ni, P, Sc, Y, Ta, a lanthanide, and a combination of any two or more of the foregoing. In some embodiments, the alkylation catalyst may further comprise a metal selected from the group consisting of Cu, Ag, Au, Pt, Ni, Fe, Co, Ru, Zn, Cd, Ga, In, Rh, Pd, Ir, Re, Mn, Cr, Mo, W, Sn, Os, an alloy of any two or more of the foregoing, and a combination of any two or more of the foregoing.

In some embodiments, the alkylation catalyst may comprise a bifunctional pentasil ring-containing aluminosilicate zeolite. In some embodiments, the alkylation catalyst may further comprise a modifier selected from the group consisting of Ga, In, Zn, Fe, Mo, Ag, Au, Ni, P, Sc, Y, Ta, a lanthanide, and a combination of any two or more of the foregoing. In some embodiments, the alkylation catalyst may further comprise a metal selected from the group consisting of Cu, Ag, Au, Pt, Ni, Fe, Co, Ru, Zn, Cd, Ga, In, Rh, Pd, Ir, Re, Mn, Cr, Mo, W, Sn, Os, an alloy of any two or more of the foregoing, and a combination of any two or more of the foregoing. In one version, the dehydration catalyst and the alkylation catalyst may be atomically identical.

The alkylation reaction may be conducted at a temperature where the thermodynamics are favorable. In general, the alkylation temperature may range between about −20° C. and about 300° C., and the alkylation pressure may range between about 1 bar (absolute) and about 80 bar. In some embodiments, the alkylation temperature may range between about 100° C. and about 300° C. In another version, the alkylation temperature may range between about 0° C. and about 100° C. In yet other embodiments, the alkylation temperature may range between about 0° C. and about 50° C. In still other embodiments, the alkylation temperature may range between about 70° C. and about 250° C., and the alkylation pressure may range between about 5 bar and about 80 bar. In some embodiments, the alkylation catalyst may comprise a mineral acid or a strong acid. In other embodiments, the alkylation catalyst may comprise a zeolite and the alkylation temperature may be greater than about 100° C.

In some embodiments, an olefinic oligomerization reaction may conducted. The oligomerization reaction may be carried out in any suitable reactor configuration. Suitable configurations may include, but are not limited to, batch reactors, semi-batch reactors, or continuous reactor designs such as, for example, fluidized bed reactors with external regeneration vessels. Reactor designs may include, but are not limited to tubular reactors, fixed bed reactors, or any other reactor type suitable for carrying out the oligomerization reaction. In some embodiments, a continuous oligomerization process for the production of diesel and jet fuel boiling range hydrocarbons may be carried out using an oligomerization reactor for contacting an olefinic feed stream comprising short chain olefins having a chain length of from 2 to 8 carbon atoms with a zeolite catalyst under elevated temperature and pressure so as to convert the short chain olefins to a fuel blend in the diesel boiling range. The oligomerization reactor may be operated at relatively high pressures of about 20 bar to about 100 bar, and temperatures ranging between about 150° C. and about 300° C., preferably between about 200° C. to 250° C.

The resulting oligomerization stream results in a fuel blend that may have a wide variety of products including products comprising C5 to C24 hydrocarbons. Additional processing may be used to obtain a fuel blend meeting a desired standard. An initial separation step may be used to generate a fuel blend with a narrower range of carbon numbers. In some embodiments, a separation process such as a distillation process may be used to generate a fuel blend comprising C12 to C24 hydrocarbons for further processing. The remaining hydrocarbons may be used to produce a fuel blend for gasoline, recycled to the oligomerization reactor, or used in additional processes. For example, a kerosene fraction may be derived along with the diesel fraction and may either be used as an illuminating paraffin, as a jet fuel blending component in conventional crude or synthetic derived jet fuels, or as reactant (especially C10 to C13 fraction) in the process to produce LAB (Linear Alkyl Benzene). The naphtha fraction, after hydroprocessing, may be routed to a thermal cracker for the production of ethylene and propylene or routed to a catalytic cracker to produce ethylene, propylene, and gasoline.

Additional processes may be used to treat the fuel blend to remove certain components or further conform the fuel blend to a diesel or jet fuel standard. Suitable techniques may include hydrotreating to remove any remaining oxygen, sulfur, or nitrogen in the fuel blend. Hydrogenation may be carried after the hydrotreating process to saturate at least some olefinic bonds. Such hydrogenation may be performed to conform the fuel blend to a specific fuel standard (e.g., a diesel fuel standard or a jet fuel standard). The hydrogenation step of the fuel blend stream may be carried out according to the known procedures, in a continuous or batchwise manner.

To facilitate a better understanding of the present invention, the following examples of preferred embodiments are given. In no way should the following examples be read to limit, or to define, the scope of the invention.

EXAMPLES

Unless otherwise indicated below, reactions were conducted in a Parr5000 HASTELLOY multireactor unit containing 6×75 mL reactors operated in parallel at pressures up to 135 bar and temperatures up to 275° C., stirred by magnetic stir bar. Alternate studies were conducted in 100 mL Parr 4590 reactors, with mixing by a top-driven stir shaft impeller, which was also capable of attaining a pressure of 135 bar and a temperature of 275° C. Liquid chromatographic analyses were conducted by HPLC using a Bio-Rad Aminex HPX-87H column (300 mm×7.8 mm) at a flow rate of 0.6 mL/min 5 mM sulfuric acid in water and an oven temperature of 30° C. The run time was 70 minutes.

Gas chromatographic analyses were conducted using a 60 m×0.32 mm ID DB-5 column of 1 µm thickness, with 50:1 split ratio, 2 ml/min helium flow, and column oven temperature of 40° C. for 8 minutes, followed by a ramp to 285° C. at 10° C./min and a hold time of 53.5 minutes. The injector temperature was set at 250° C., and the detector temperature was set at 300° C.

Example 1

Paste Formation at High Loadings of Cellulosic Biomass Solids. 2.08 grams of finely ground pine wood sawdust containing 11.3% moisture was added to 25.5 grams of deionized water in a graduated cylinder. After mixing and allowing the wood to equilibrate, 10.4 grams of water was removed by syringe from the top of the wood bed. The cylinder was then tilted to decant additional water, but only one gram of additional water was removed, yielding a final water to dry solids ratio of 8.3:1. 0.1 grams of a slurry catalyst having a particle size of 1-25 microns was added, and the cylinder was mixed by inverting several times. Virtually no mixing of the slurry catalyst with the wood was observed due to paste formation by the finely divided wood.

Example 2

Role of Biomass Particulate Size on Digestion Rate. Parallel Parr 5000 reactors were loaded with 20.0 grams of 50% 2-propanol in deionized water containing 0.05 grams of sodium carbonate. 2.70 grams of soft wood pine chips containing 39% moisture was added to each reactor. In the first reactor, a single 1 inch×1 inch×3 mm wood chip was added. In the second reactor, the pine wood was hand clipped to several ¼ inch×¼ inch×3 mm mini chips. In the third reactor, the pine wood was ground in a coffee grinder to a nominal 3 mm maximum size.

All three reactors were pressurized to 51 bar with $H_2$ and heated to 190° C. for one hour before ramping to 240° C. to complete a 5 hour cycle. The reactor contents were filtered by Whatman GF/F filter paper, and the paper with solids was dried in a vacuum oven overnight at 90° C. 78% by weight of wood from the first reactor dissolved, and the smaller wood chips in the other two reactors gave 72% by weight dissolution, on a water-free basis. It is believed that these results are essentially the same within experimental error and that the digestion rate is not significantly impacted by the wood chip size.

Example 3

Digestion of Cellulosic Biomass in the Presence of a Bottom-Loaded Slurry Catalyst. The lower 2.25-inch zone of a 12.5 inch×0.5-inch O.D. (0.402-inch I.D) digester tube was packed with ⅛-inch ceramic spheres (Denstone), followed by 0.7-inches of 14×40 mesh filter sand. On the sand was placed 0.604 grams of sulfided cobalt molybdate catalyst (DC2534, Criterion Catalyst & Technologies L.P) containing 1-10% cobalt oxide and molybdenum trioxide (up to 30 wt %) on alumina crushed to a particle size of less than 100 µm. The catalyst was previously sulfided as described in United States Patent Application publication 20100236988. The tube was then packed with 4.00 grams of southern pine wood chips having a nominal dimension of 3 mm×5 mm×5 mm, thereby forming an 8.7 inch chip bed.

The digestion unit was filled from the bottom with 50% 2-propanol/deionized water, buffered with 0.3 wt % sodium carbonate. Addition of the digestion solvent was continued until void spaces in the chip bed were filled and a liquid layer more than 0.5 inches above the bed was obtained. The ratio of solvent to dry wood in the packed bed was less than 5.8:1. Liquid flow was then terminated. The digestion unit was then pressured to 70 bar with $H_2$, and a continuous flow of hydrogen was added from the bottom of the digestion unit and vented from the top at a flow rate of 95 ml/min at standard room temperature and atmospheric pressure (STP). This flow rate corresponded to a superficial linear velocity of hydrogen flow of 0.05 cm/sec through the digestion unit. The bottom entry port was tubing having a nominal 3 mm O.D. (2 mm I.D.), thereby acting as a nozzle for gas bubble formation.

The digestion unit was then heated to 190° C. for 1.5 hours, followed by heating to 240° C. for 3.5 hours. At the end of the experiment, 9.24 grams of liquid product was drained from the digestion unit. 7.8 grams of condensed liquid product was also collected from overflow carried with the hydrogen sparge. Analysis of the liquid product indicated a mixture of oxygenated products (including monohydric alcohols and glycols) at 82% of the expected theoretical yield based on the amount of carbohydrates present in the initial wood charge. There were no remaining wood solids at the end of the digestion period.

Example 4

Digestion of Cellulosic Biomass in the Presence of a Top-Loaded Slurry Catalyst. The experiment of Example 3 was repeated, except the 0.600 grams of the catalyst was placed on top of the chip bed, rather than beneath it. The initial ratio of solvent to dry wood was less than 5.5:1. After digestion, 10.1 grams of liquid product was drained from the digestion unit, and 7.28 grams of condensed liquid product was collected from overflow. Again, no observable wood solids remained at the end of the digestion period. In contrast to catalyst loading beneath the chip bed, which produced a relatively high yield, the yield with catalyst loading on the top of the chip bed produced a yield that was only 28% of the theoretical yield. LC/MS analysis of the liquid product indicated the possible presence of oligomeric byproducts having a molecular weight greater than 300 and too high for detection by gas chromatography.

Example 5

Digestion of Cellulosic Biomass in the Presence of a Bottom-Loaded Slurry Catalyst at a Lower Pressure. The experiment of Example 3 was repeated using 6.05 grams of southern pine chips and 15.4 mL of digestion solvent, added from the bottom, to fully cover the chip bed. In this case, the digestion unit was pressurized only to 37 bar, relative to an estimated solvent vapor pressure of about 32 bar. The vented hydrogen flow rate was 97 mL/min, and a digestion solvent of 50% 2-propanol in deionized water was co-fed from the bottom of the digestion unit at a flow rate of 0.05 mL/min. The digestion unit was heated to 190° C. for 1.5 hours, followed by heating to 240° C. for 5 hours, with hydrogen and digestion solvent flow rates maintained at the same levels. 18.53 grams of liquid product was drained from overflow, and 8.17 grams was drained from the digestion unit at the end of the run. 5.167 grams of wood chips were required to repack the digestion unit to its previous level. This result indicated a minimum of 85% digestion under the digestion conditions. Gas chromatographic analysis indicated only 31% conversion to the desired products. Comparison of this result with Example 3 showed that increased hydrogen pressure promoted stabilization of the soluble carbohydrates in the form of a higher yield.

Example 6

Digestion of Cellulosic Biomass in the Presence of a Bottom-Loaded Slurry Catalyst with No Hydrogen Flow. The experiment of Example 5 was repeated with initial pressurization with 70 bar hydrogen, but only maintaining digestion solvent flow through the cellulosic biomass and no hydrogen flow. At the end of the run, 17.45 grams of liquid product was drained from overflow, and 7.4 grams of liquid product was drained from the digestion unit. 8 ml of undigested wood was also collected after the run, indicating about 50% conversion. Gas chromatographic analysis indicated about 27% yield of the desired reaction product in the liquid product. Again, poorer stabilization occurred when the amount of available hydrogen was reduced by termination of its flow.

Example 7

Digestion of Cellulosic Biomass in the Absence of a Slurry Catalyst. The experiment of Example 3 was repeated after addition of 6.76 grams of pine chips, but without including the slurry catalyst. Although all the wood charge was digested in 6.5 hours, GC analysis indicated that only 3% of the desired reaction product formed.

Example 8

Digestion of Cellulosic Biomass in the Presence of a Bottom-Loaded Slurry Catalyst at Room Temperature with Gas and Liquid Flow. The experiment of Example 3 was repeated with the addition of 5.29 grams of southern pine wood chips, but the digestion unit was maintained at 23.5° C. for the duration of exposure. 7.597 grams of liquid product was drained from the digestion unit at the end of the run. Analysis of the chip bed following removal of the liquid product indicated uniform dispersal of the catalyst throughout the height of the cellulosic biomass bed, thereby showing that gas and liquid flow can be effective for distributing the slurry catalyst in the cellulosic biomass solids.

Example 9

Digestion of Cellulosic Biomass in the Presence of a Bottom-Loaded Slurry Catalyst at Room Temperature with Liquid Flow Only. The experiment of Example 8 was repeated after refilling with 7.13 grams of pine chips, except upflow of hydrogen was not used and only 0.05 mL/min upflow of the digestion solvent was present. 1.36 grams of liquid product was drained from overflow and 10.67 grams of liquid product was obtained from the digestion unit. Analysis of the chip bed following removal of the liquid product showed that the catalyst was only distributed in approximately the lower 20% of the chip bed, with no catalyst found distributed in the upper portions of the wood chip charge.

Example 10

Determination of Minimum Gas Velocity Needed for Fluidization of Slurry Catalyst. A 100 mL graduated cylinder was filled with 1 gram of nominal 1-25 μm NiMo/alumina slurry catalyst and 50 grams of deionized water. A fritted sparging stone (ACE Glass) was placed at the bottom of the graduated cylinder and connected to an N2 supply using ⅛-inch Teflon tubing. The $N_2$ flow rate was varied to determine minimum flow rate needed to completely fluidize the slurry catalyst to the top of the liquid column. The linear velocity of gas corresponding to complete fluidization determined using this method was 0.037 cm/sec. Hydrogen gas flow, when used in the previous examples, exceeded this minimum velocity for fluidization and suspension of the catalyst.

Therefore, the present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope and spirit of the present invention. The invention illustratively disclosed herein suitably may be practiced in the absence of any element that is not specifically disclosed herein and/or any optional element disclosed herein. While compositions and methods are described in terms of "comprising," "containing," or "including" various components or steps, the compositions and methods may also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces. If there is any conflict in the usages of a word or term in this specification and one or more patent or other documents that may be incorporated herein by reference, the definitions that are consistent with this specification should be adopted.

We claim:

1. A method comprising:
   providing cellulosic biomass solids and a slurry catalyst in a hydrothermal digestion unit, the slurry catalyst being capable of activating molecular hydrogen, wherein the slurry catalyst is bottom-loaded to the hydrothermal digestion unit;
   distributing the slurry catalyst within the cellulosic biomass solids using upwardly directed fluid flow velocity sufficient to transport at least a portion of the slurry catalyst through the cellulosic biomass solids in the hydrothermal digestion unit;
   heating the cellulosic biomass solids in the hydrothermal digestion unit in the presence of the slurry catalyst, a digestion solvent, and molecular hydrogen, thereby forming a liquor phase comprising soluble carbohydrates; and
   performing a first catalytic reduction reaction on the soluble carbohydrates within the hydrothermal digestion unit, thereby at least partially forming a reaction product comprising a triol, a diol, a monohydric alcohol, or any combination thereof in the hydrothermal digestion unit.

2. The method of claim 1, wherein the slurry catalyst is provided in the hydrothermal digestion unit before the cellulosic biomass solids are provided.

3. The method of claim 1, wherein heating the cellulosic biomass solids takes place while the hydrothermal digestion unit is in a pressurized state.

4. The method of claim 3, wherein the cellulosic biomass solids are continuously or semi-continuously provided to the hydrothermal digestion unit while the hydrothermal digestion unit is in the pressurized state.

5. The method of claim 1, wherein distributing the slurry catalyst takes place before forming the liquor phase comprising soluble carbohydrates.

6. The method of claim 1, wherein the upwardly directed fluid flow comprises one or more upwardly directed fluid streams, the one or more upwardly directed fluid streams comprising a gas stream, a liquid stream, or any combination thereof.

7. The method of claim 6, wherein the gas stream comprises a stream of molecular hydrogen and the liquid stream comprises a stream of the digestion solvent.

8. The method of claim 1, wherein the digestion solvent comprises the reaction product.

9. The method of claim 1, wherein at least a portion of the slurry catalyst is fluidly suspended in the digestion solvent by the upwardly directed fluid flow.

10. The method of claim 1, wherein at least a portion of the slurry catalyst is transported through the cellulosic biomass solids by the upwardly directed fluid flow.

11. The method of claim 10, further comprising:
    circulating the slurry catalyst external to the hydrothermal digestion unit and returning the slurry catalyst thereto.

12. The method of claim 11, wherein the slurry catalyst is returned to the bottom of the hydrothermal digestion unit.

13. The method of claim 11, wherein the slurry catalyst is circulated at a velocity such that a concentration of the slurry catalyst in the liquor phase is substantially homogeneous.

14. The method of claim 11, further comprising:
    forming cellulosic biomass fines within the liquor phase; and
    circulating at least a portion of the cellulosic biomass fines external to the hydrothermal digestion unit.

15. The method of claim 1, further comprising:
    transferring at least a portion of the liquor phase from the hydrothermal digestion unit; and
    performing a second catalytic reduction reaction thereon so as to further form the reaction product.

16. The method of claim 1, further comprising:
    catalytic reforming the reaction product into a biofuel.

17. The method of claim 1, wherein the slurry catalyst comprises a poison-tolerant catalyst.

18. A method comprising:
    providing cellulosic biomass solids and a slurry catalyst in a hydrothermal digestion unit, the slurry catalyst being capable of activating molecular hydrogen, wherein the slurry catalyst is bottom-loaded to the hydrothermal digestion unit;
    heating the cellulosic biomass solids in the hydrothermal digestion unit in the presence of molecular hydrogen while forcing the slurry catalyst to circulate through the cellulosic biomass solids in a digestion solvent, thereby forming a liquor phase comprising soluble carbohydrates; and
    performing a first catalytic reduction reaction on the soluble carbohydrates within the hydrothermal digestion unit, thereby at least partially forming a reaction product comprising a triol, a diol, a monohydric alcohol, or any combination thereof in the hydrothermal digestion unit.

19. The method of claim 18, wherein the slurry catalyst is provided in the hydrothermal digestion unit before the cellulosic biomass solids are provided.

20. The method of claim 18, wherein heating the cellulosic biomass solids takes place while the hydrothermal digestion unit is in a pressurized state.

21. The method of claim 20, wherein the cellulosic biomass solids are continuously or semi-continuously provided to the hydrothermal digestion unit while the hydrothermal digestion unit is in the pressurized state.

22. The method of claim 18, wherein the slurry catalyst is circulated through the cellulosic biomass solids using upwardly directed fluid flow in the hydrothermal digestion unit.

23. The method of claim 22, wherein the upwardly directed fluid flow comprises one or more upwardly directed fluid streams, the one or more upwardly directed fluid streams comprising a stream of the digestion solvent.

24. The method of claim 23, wherein the one or more upwardly directed fluid streams comprises a stream of molecular hydrogen.

25. The method of claim 22, wherein the slurry catalyst is circulated external to the hydrothermal digestion unit and returned thereto.

26. The method of claim 25, wherein the slurry catalyst is returned to the bottom of the hydrothermal digestion unit.

27. The method of claim 25, further comprising:
    forming cellulosic biomass fines within the liquor phase; and
    circulating at least a portion of the cellulosic biomass fines external to the hydrothermal digestion unit.

28. The method of claim 22, wherein the slurry catalyst is circulated through the cellulosic biomass solids at a velocity such that a concentration of the slurry catalyst in the liquor phase is substantially homogeneous.

29. The method of claim 18, further comprising:
    transferring at least a portion of the liquor phase from the hydrothermal digestion unit; and performing a second catalytic reduction reaction thereon so as to further form the reaction product.

30. The method of claim 18, further comprising:
catalytic reforming the reaction product into a biofuel.

31. The method of claim 18, wherein the slurry catalyst comprises a poison-tolerant catalyst.

* * * * *